(12) United States Patent
Kleen et al.

(10) Patent No.: US 7,247,173 B2
(45) Date of Patent: *Jul. 24, 2007

(54) TINTING AGENT IN TUBES

(75) Inventors: Astrid Kleen, Hamburg (DE); Mustafa Akram, Hamburg (DE); Susanne Bietz, Elmshorn (DE); Stefan Hoepfner, Hamburg (DE); Hartmut Manneck, Klein Wesenberg (DE); Maureen Rippe, Schneeverdingen (DE)

(73) Assignee: Henkel Kommandit Gesellschaft auf Aktien, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/454,706

(22) Filed: Jun. 15, 2006

(65) Prior Publication Data

US 2006/0288496 A1 Dec. 28, 2006

Related U.S. Application Data

(63) Continuation of application No. PCT/EP2004/013929, filed on Dec. 8, 2004.

(30) Foreign Application Priority Data

Dec. 17, 2003 (DE) ................. 103 59 538

(51) Int. Cl.
*A61K 7/13* (2006.01)
(52) U.S. Cl. .................. 8/405; 8/425; 8/437; 8/451; 8/466; 8/552; 8/632; 8/646
(58) Field of Classification Search .......... 8/405, 8/425, 437, 451, 466, 552, 632, 646
See application file for complete search history.

(56) References Cited

U.S. PATENT DOCUMENTS

| | | | |
|---|---|---|---|
| 2,019,576 A | 11/1935 | Mikaelson | |
| 3,753,968 A | 8/1973 | Ward | |
| 3,931,912 A | 1/1976 | Hsiung | |
| 4,184,844 A | 1/1980 | Grollier | |
| 4,237,253 A | 12/1980 | Jacquet | |
| 4,294,293 A | 10/1981 | Lorenz | |
| 4,324,780 A | 4/1982 | Jacquet | |
| 4,393,886 A | 7/1983 | Strasilla | |
| 4,725,282 A | 2/1988 | Hoch | |
| 4,814,101 A | 3/1989 | Schieferstein | |
| 4,865,774 A | 9/1989 | Fabry | |
| 4,931,218 A | 6/1990 | Schenker | |
| 5,061,289 A | 10/1991 | Clausen | |
| 5,136,093 A | 8/1992 | Smith | |
| 5,294,726 A | 3/1994 | Behler | |
| 5,380,340 A | 1/1995 | Neunhoeffer | |
| 5,480,459 A | 1/1996 | Mager | |
| 5,534,267 A | 7/1996 | Neunhoeffer | |
| 5,766,576 A | 6/1998 | Lowe | |
| 5,773,595 A | 6/1998 | Weuthen | |
| 6,099,592 A | 8/2000 | Vidal | |
| 6,284,003 B1 | 9/2001 | Rose | |
| 6,485,528 B1* | 11/2002 | Bartels et al. ................. 8/405 |
| 2003/0106167 A1 | 6/2003 | Rose | |
| 2003/0150069 A1 | 8/2003 | Kleen | |
| 2003/0167578 A1 | 9/2003 | Naumann | |
| 2004/0049860 A1 | 3/2004 | Cottard | |

FOREIGN PATENT DOCUMENTS

| | | |
|---|---|---|
| DE | 1 942 570 | 3/1970 |
| DE | 23 59 399 | 6/1975 |
| DE | 28 17 369 | 10/1978 |
| DE | 28 27 610 | 1/1980 |
| DE | 31 39 438 | 4/1983 |
| DE | 37 23 354 | 1/1989 |
| DE | 37 25 030 | 2/1989 |
| DE | 38 43 892 | 6/1990 |
| DE | 39 26 344 | 2/1991 |
| DE | 39 29 973 | 3/1991 |
| DE | 41 33 957 | 4/1993 |
| DE | 44 13 686 | 10/1995 |
| DE | 44 13 868 | 10/1995 |
| DE | 195 43 988 | 5/1997 |
| DE | 197 56 454 | 6/1999 |
| DE | 199 45 486 | 3/2001 |
| DE | 101 62 640 | 7/2003 |
| DE | 102 40 757 | 7/2003 |
| EP | 0 047 714 | 3/1982 |
| EP | 0 217 274 | 4/1987 |
| EP | 0 283 817 | 9/1988 |
| EP | 0 671 161 | 9/1995 |
| EP | 0 740 931 | 11/1996 |

(Continued)

OTHER PUBLICATIONS

Verlag Marcel Dekker INc., New York, Basle, 1986 (Science of Hair Care, Chapter 7, pp. 248-250; direct dyes).*
U.S. Appl. No. 11/455,434, filed Jun. 19, 2006, Kleen.
U.S. Appl. No. 11/471,101, filed Jun. 19, 2006, Kleen.
Gutcho, M.H., ed., "Inorganic Pigments: Manufacturing Processes," Chemical Technology review No. 166, pp. 161-173, (1980) (ISBN: 0-8155-0811-5).

(Continued)

*Primary Examiner*—Eisa Elhilo
(74) *Attorney, Agent, or Firm*—John E. Drach

(57) ABSTRACT

Keratinic fibers are dyed with a two-component agent for tinting and/or dyeing keratinic fibers comprising a first preparation (A) comprising at least one direct-absorbing dye and/or at least one precursor of a nature-analogous dye, and a second preparation (B) containing at least one conditioning substance, wherein the two preparations are packaged separately from one another in the chambers of a two-chamber tube. The chamber openings in the tube are oriented in such a way that the contents of each of the chambers are emitted simultaneously into a common space.

19 Claims, No Drawings

FOREIGN PATENT DOCUMENTS

| | | |
|---|---|---|
| EP | 0 998 908 | 5/2000 |
| GB | 1 026 978 | 4/1966 |
| GB | 1 153 196 | 5/1969 |
| GB | 1 289 712 | 9/1972 |
| GB | 2 104 091 | 3/1983 |
| JP | 03-225052 | 10/1991 |
| WO | WO 86/00223 | 1/1986 |
| WO | WO 02/13829 | 8/1992 |
| WO | WO 93/23006 | 11/1993 |
| WO | WO 94/08969 | 4/1994 |
| WO | WO 94/08970 | 4/1994 |
| WO | WO 96/02162 | 2/1996 |
| WO | WO 96/15765 | 5/1996 |
| WO | WO 00/47714 | 8/2000 |
| WO | WO 01/97756 | 12/2001 |
| WO | WO 02/17274 | 2/2002 |
| WO | WO 02/45673 | 6/2002 |
| WO | WO 02/083817 | 10/2002 |
| WO | WO 03/089330 | 10/2003 |

OTHER PUBLICATIONS

Buxbaum, G., ed., "Industrial inorganic pigments, 2 edition", Weinheim, VCH, pp. 211-231 (1998).

Zviak, C., ed., The Science of Hair Care, Chapter 7, pp. 248-250 vol. 7 "Dermatologie")(1986).

Zviak, C., ed., The Science of Hair Care, Chapter 8, pp. 264-267 vol. 7 "Dermatologie")(1986).

Website printout, Enterprise and Industry, "Cosmetics—Introduction", from the European Commission, dated Jan. 23, 2006.

Schrader, K-H., "Grundlagen und Rezepturen der Kosmetika," 2nd edition, table of contents Huthig Verlag, Heidelberg, (1989).

"International Cosmetic Ingredient Dictionary and Handbook," Seventh Ed., The Cosmetic, Toiletry and Fragrance Assn. Washington DC (1997).

Guideline for declaring the contents of cosmetic agents, published by Assn. of Personal Hygiene and Washing Agents Industry (1996).

Copending U.S. Appl. No. 11/508,482.

* cited by examiner

TINTING AGENT IN TUBES

CROSS REFERENCE TO RELATED APPLICATIONS

This application is a continuation under 35 U.S.C. § 365(c) and 35 U.S.C. § 120 of International Application PCT/EP2004/013929, filed Dec. 8, 2004. This application also claims priority under 35 U.S.C. § 119 of DE 103 59, 538.4, filed Dec. 17, 2003. Each application is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to two-component agents for tinting or dyeing keratinic fibers, said agents being packaged in a two-chamber tube; to a corresponding two-chamber tube; and to a method for tinting and/or dyeing keratinic fibers with the aid of this two-component agent.

Preparations for tinting and dyeing hair are an important type of cosmetic agent. They can serve to tone the natural hair color to a greater or lesser degree according to the corresponding person's wishes, to achieve an entirely different hair color, or to conceal undesired colors such as, for example, gray tints. Depending on the desired color and the durability of the coloring, usual hair-coloring agents are formulated on the basis either of oxidant dyes or of direct-absorbing dyes. Combinations of oxidizing dyes and direct-absorbing dyes are also often used to achieve specific shades.

Coloring agents based on oxidizing dyes result in brilliant and permanent colors. They require, however, the use of strong oxidizing agents such as, for example, hydrogen peroxide solutions. Such coloring agents contain oxidizing dye precursors, so-called developer components, and coupler components. Under the influence of the oxidizing agents or atmospheric oxygen, the developer components form, among one another or by coupling to one or more coupler components, the actual dyes.

Coloring agents based on direct-absorbing dyes require no oxidizing agents, and can be formulated at pH values in the region of neutrality, but yield colors that are less permanent. In addition, the ability of the dye molecules to be absorbed onto the hair, and the luster of the colored hair, may not be entirely satisfactory in many cases.

Not least, the large amount of stress on the hair resulting from such color-modifying treatments, as well as permanent waves, hair washing with shampoos, and environmental stresses, increase the importance of conditioning products having effects that last as long as possible. Such conditioning agents influence the natural structure and properties of the hair. Subsequent to a treatment with a conditioning agent, for example, the wet and dry combability of the hair and its stability, body, and fullness can be optimized, or the hair can be protected from increasing splitting.

Therefore, it has been usual for some time to subject the hair to a specific post-treatment. In this, the hair is treated, usually in the form of a rinse, with specific active substances, for example, quaternary ammonium salts or specific polymers. Depending on the formulation, this treatment improves the hair's combability, cohesion and fullness, and decreases splitting.

The active substances that are available typically act preferentially on the hair surface. Active substances are known, for example, that impart luster, stability, fullness, or better wet or dry combability to the hair, or that prevent splitting. Just as significant as the external appearance of the hair, however, is the internal structural cohesion of the hair fibers, which can be greatly influenced especially by oxidizing and reducing processes such as dyeing and permanent waves. Active substances have also recently been proposed that can counteract, in sustained fashion, this change in the internal structure of the fibers.

Very recently, so-called combination preparations have been developed in order to reduce the complexity of the usual multi-step methods, in particular in a context of direct application by users. In addition to the usual components for tining and/or dyeing the hair, these preparations contain active substances that were previously reserved for hair post-treatment agents. The consumer thus eliminates one application step. Packaging outlay is at the same time reduced, since one less product is used.

The known active substance in some cases has the disadvantage, however, that they cannot be formulated in stable fashion in the tinting agents.

BRIEF SUMMARY OF THE INVENTION

Surprisingly, it has now been discovered, that stable tinting agents with outstanding conditioning effectiveness can be obtained when an agent containing at least one direct-absorbing dye and/or one precursor of a nature-analogous dye, and an agent containing at least one conditioning component, are packaged separately from one another in a two-chamber tube.

A first subject of the present invention is therefore two-component agents for tinting and/or dying keratinic fibers, said agents being made up of a first preparation (A) containing at least one direct-absorbing dye and/or at least one precursor of a nature-analogous dye, and a second preparation (B) containing at least one conditioning substance, the two preparations being packaged separately from one another in the chambers of a two-chamber tube.

The two-component agents according to the present invention are characterized by outstanding conditioning and dyeing performance, and high stability. The two-component agent also provides assurance that the consumer applies the components in the mixing ratio specified by the manufacturer. On the one hand, this enhances product safety, and on the other hand, guarantees that the product delivers the desired performance.

BRIEF DESCRIPTION OF THE SEVERAL VIEWS OF THE DRAWING(S)

Not Applicable

DETAILED DESCRIPTION OF THE INVENTION

In a first preferred embodiment, preparation (A) of the two-component agent according to the present invention contains at least one direct-absorbing dye. The direct-absorbing dyes are preferably selected from the nitrophenylendiamines, the nitroaminophenols, the azo dyes, the anthraquinones, or the indophenols. Particularly preferred direct-absorbing dyes are the compounds known under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-1-hydroxy-4-nitrobenzene. In addition, it can be preferred according to the present invention for the agents to contain at least one cationic direct-absorbing dye. Particularly preferred in this context are:

(a) cationic triphenylmethane dyes such as, for example, Basic Blue 7, Basic Blue 26, Basic Violet 2, and Basic Violet 14;

(b) aromatic systems that are substituted with a quaternary nitrogen group, such as, for example, Basic Yellow 57, Basic Red 76, Basic Blue 99, Basic Brown 16 and Basic Brown 17; and (c) direct-absorbing dyes that contain at least one heterocycle that comprises at least one quaternary nitrogen atom, such as those recited, for example, in EP-A2-992 908, to which reference is explicitly made at this junction, in claims 6 to 11.

Preferred cationic direct-absorbing dyes of group (c) are, in particular, the following compounds:

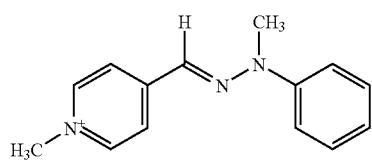

(DZ1)

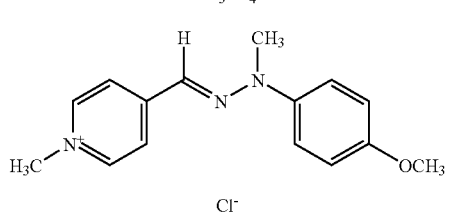

(DZ2)

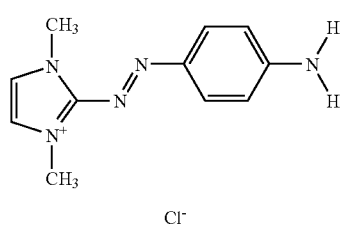

(DZ3)

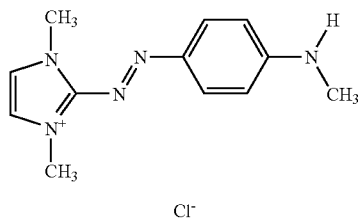

(DZ4)

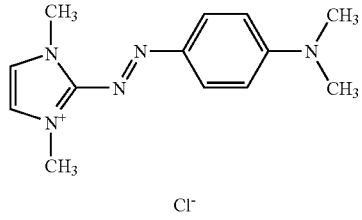

(DZ5)

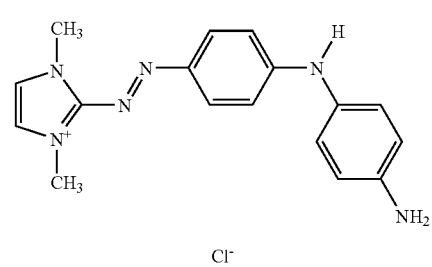

(DZ6)

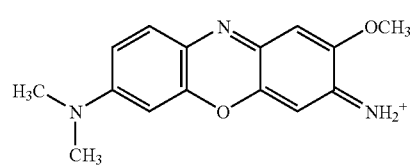

(DZ7)

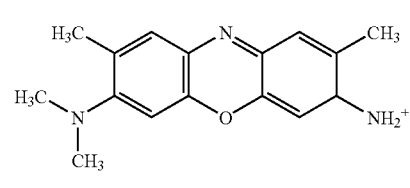

(DZ8)

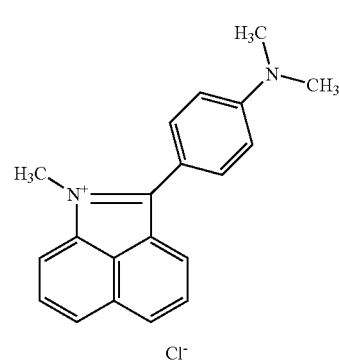

(DZ9)

The compounds of formulas (DZ1), (DZ3), and (DZ5), which are also known by the designations Basic Yellow 87, Basic Orange 31, and Basic Red 51, are very particularly preferred cationic direct-absorbing dyes of group (c).

The cationic direct-absorbing dyes marketed under the trademark Arianor® are likewise very particularly preferred cationic direct-absorbing dyes according to the present invention.

Additionally, the preparations according to the present invention can also contain naturally occurring direct-absorbing dyes, for example, such as those contained in red henna, neutral henna, black henna, chamomile blossoms, sandalwood, black tea, buckthorn bark, salvia, logwood, madder root, catechu, Spanish cedar, and alkanna root.

The two-component agents according to the present invention contain the direct-absorbing dyes preferably in a quantity from 0.01 to 20 wt % based on the entire application preparation, i.e. based on the sum of preparations (A) and (B).

In the context of a second preferred embodiment, the two-component agents according to the present invention contain, in preparation (A), at least one precursor of a nature-analogous dye.

Indoles and indolines that comprise at least one hydroxy or amino group, preferably as a substituent on the six-membered ring, are preferred for use as precursors of nature-analogous dyes. These groups can carry further substituents, e.g., in the form of an etherification or esterification of the hydroxy group or an alkylation of the amino group. In a preferred embodiment, the two-component agents therefore contain at least one indole derivative and/or one indoline derivative.

Particularly suitable as precursors of nature-analogous hair dyes are derivatives of 5,6-dihydroxyindoline of formula (Ia):

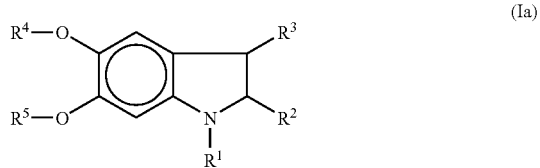

in which, independently of one another:
R$^1$ denotes hydrogen, a C$_1$-C$_4$ alkyl group, or a C$_1$-C$_4$ hydroxyalkyl group,
R$^2$ denotes hydrogen or a —COOH group, such that the —COOH group can also be present as a salt having a physiologically acceptable cation,
R$^3$ denotes hydrogen or a C$_1$-C$_4$ alkyl group,
R$^4$ denotes hydrogen, a C$_1$-C$_4$ alkyl group, or a —CO—R$^6$ group in which R$^6$ denotes a C$_1$-C$_4$ alkyl group, and
R$^5$ denotes one of the groups listed under R$^4$, as well as physiologically acceptable salts of these compounds with an organic or inorganic acid.

Examples of the C$_1$-C$_4$ alkyl groups mentioned as substituents in the compounds according to the present invention are the methyl, ethyl, propyl, isopropyl, and butyl groups. Ethyl and methyl are preferred alkyl groups. Additionally, a hydroxymethyl, 2-hydroxyethyl, 3-hydroxypropyl, or 4-hydroxybutyl group may be mentioned as preferred examples of a C$_1$-C$_4$ monohydroxyalkyl group. A 2-hydroxyethyl group is particularly preferred.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, as well as 6-hydroxy-indoline, 6-aminoindoline, and 4-aminoindoline.

Particularly to be emphasized within this group are N-methyl-5,6-dihydroxyindoline, N-ethyl-5,6-dihydroxyindoline, N-propyl-5,6-dihydroxyindoline, N-butyl-5,6-dihydroxyindoline, and in particular, 5,6-dihydroxyindoline.

Also outstandingly suitable as precursors of nature-analogous hair dyes are derivatives of 5,6-dihydroxyindole of formula (Ib):

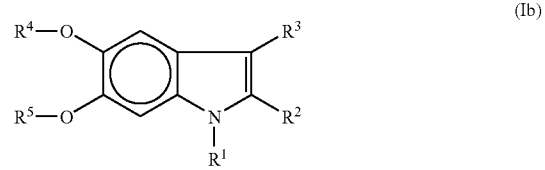

in which, independently of one another:
R' denotes hydrogen, a C$_1$-C$_4$ alkyl group, or a C$_1$-C$_4$ hydroxyalkyl group,
R$^2$ denotes hydrogen or a —COOH group, such that the —COOH group can also be present as a salt having a physiologically acceptable cation,
R$^3$ denotes hydrogen or a C$_1$-C$_4$ alkyl group,
R$^4$ denotes hydrogen, a C$_1$-C$_4$ alkyl group, or a —CO—R$^6$ group in which R$^6$ denotes a C$_1$-C$_4$ alkyl group, and
R$^5$ denotes one of the groups listed under R$^4$, as well as physiologically acceptable salts of these compounds with an organic or inorganic acid.

Examples of the C$_1$-C$_4$ alkyl groups mentioned as substituents in the compounds according to the present invention are the methyl, ethyl, propyl, isopropyl, and butyl groups. Ethyl and methyl are preferred alkyl groups. Furthermore, a hydroxymethyl, 2-hydroxyethyl, 3-hydroxypropyl, or 4-hydroxybutyl group may be mentioned as preferred examples of a C$_1$-C$_4$ monohydroxyalkyl group. A 2-hydroxyethyl group is particularly preferred.

Particularly preferred derivatives of indole are 5,6-dihydroxyindole, N-methyl-5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole, and 4-aminoindole.

To be emphasized within this group are N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives can be used in the agents according to the present invention both as free bases and in the form of their physiologically acceptable salts with inorganic or organic acids, e.g., the hydrochlorides, sulfates, and hydrobromides. The indole or indoline derivatives are contained therein usually in quantities from 0.05 to 10 wt %, preferably 0.2 to 5 wt %, in each case based on the entire application preparation.

It can be preferred according to the present invention for the indoline or indole derivative to be used in combination with at least one amino acid or one oligopeptide. The amino acid is advantageously an α-amino acid; very particularly preferred α-amino acids are arginine, ornithine, lysine, serine, and histidine, in particular arginine. According to the present invention, it is immaterial whether the amino acid is contained in preparation (A) together with the indoline or indole derivative, or the amino acid is contained in preparation (B) separately from the indoline or indole derivative.

Preparation (B) of the two-component agent according to the present invention contains, according to the present invention, at least one conditioning substance.

In the context of a first preferred embodiment, the two-component agent according to the present invention contains at least one cationic surfactant as a conditioning substance.

Cationic surfactants of the quaternary ammonium compound type, the esterquat type, and the amidoamine type are preferred according to the present invention. Preferred quaternary ammonium compounds are ammonium halides, in particular, chlorides and bromides, such as alkyltrimethylammonium chlorides, dialkyldimethylammonium chlorides, and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, as well as the imidazolium compounds known under the INCI names Quaternium-27 and Quaternium-83. The long alkyl chains of the aforesaid surfactants preferably have 10 to 18 carbon atoms.

Esterquats are known substances that contain both at least one ester function and at least one quaternary ammonium group as structural elements. Preferred esterquats are quaternized ester salts of fatty acids with triethanolamine, quaternized ester salts of fatty acids with diethanol alkylamines, and quaternized ester salts of fatty acids with 1,2-dihydroxypropyldialkylamines. Such products are marketed, for example, under the trademarks Stepantex®, Dehyquart® and Armocare®. The products Armocare® VGH-70, an N,N-bis(2-palmitoyloxyethyl)dimethylammonium chloride, and Dehyquart® F-75, Dehyquart® C-4046, Dehyquart® L80, and Dehyquart® AU-35, are examples of such esterquats.

The alkylamidoamines are usually produced by amidation of natural or synthetic fatty acids and fatty acid cuts with dialkylaminoamines. A compound from this group of substances that is particularly suitable according to the present invention is represented by the stearamidopropyldimethylamine obtainable commercially under the designation Tegoamid® S 18.

The cationic surfactants are contained in the two-component agents according to the present invention, preferably in quantities from 0.05 to 10 wt % based on the entire application preparation. Quantities from 0.1 to 5 wt % are particularly preferred.

In the context of a second preferred embodiment of the present invention, the two-component agents contain at least one conditioning polymer as a conditioning substance.

A first group of conditioning polymers is the cationic polymers. "Cationic polymers" are to be understood, according to the present invention, as polymers that comprise in the main chain and/or side chain a group that can be "temporarily" or "permanently" cationic. According to the present invention, those polymers that possess a cationic group regardless of the pH of the agent are referred to as "permanently cationic." These are, as a rule, polymers that contain a quaternary nitrogen atom, for example, in the form of an ammonium group. Preferred cationic groups are quaternary ammonium groups. In particular, those polymers in which the quaternary ammonium group is bound via a $C_{1-4}$ hydrocarbon group to a main polymer chain made up of acrylic acid, methacrylic acid, or their derivatives, have proven to be particularly suitable.

Homopolymers of the general formula (G1-I),

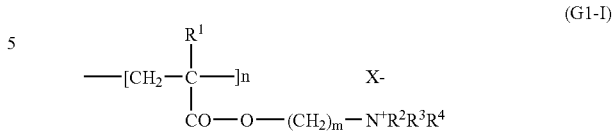

(G1-I)

in which $R^1$=—H or —$CH_3$, $R^2$, $R^3$ and $R^4$ are selected, independently of one another, from $C_{1-4}$ alkyl, $C_{2-4}$ alkenyl, or $C_{1-4}$ hydroxyalkyl groups, m=1, 2, 3 or 4, n is a natural number, preferably a natural number from 1 to 5,000, and X- is a physiologically acceptable organic or inorganic ion, as well as copolymers made up substantially of the monomer units presented in formula (G1-I) as well as nonionogenic monomer units, are particularly preferred cationic polymers. In the context of these polymers, those for which at least one of the following conditions apply are preferred according to the present invention:

$R^1$ denotes a methyl group
$R^2$, $R^3$ and $R^4$ denote methyl groups
m has the value of 2.

Possibilities as physiologically acceptable counterions $X^-$ are, for example, halide ions, sulfate ions, phosphate ions, methosulfate ions, and organic ions such as lactate, citrate, tartrate, and acetate ions. Halide ions, in particular, chloride, are preferred.

A particularly suitable homopolymer is the poly(methacryloyloxyethyltrimethylammonium chloride) (crosslinked, if desired) having the INCI name Polyquaternium-37. The crosslinking can be accomplished, if desired, with the aid of multiply olefinically unsaturated compounds, for example, divinylbenzene, tetraallyloxyethane, methylene bisacrylamide, diallyl ether, polyallylpolyglyceryl ether, or allyl ethers of sugars or sugar derivatives such as erythritol, pentaerythritol, arabitol, mannitol, sorbitol, sucrose, or glucose. Methylene bisacrylamide is a preferred cross-linking agent.

The homopolymer is preferably used in the form of a nonaqueous polymer dispersion that should comprise a polymer proportion not less than 30 wt %. Such polymer dispersions are obtainable commercially under the designations Salcare® SC 95 (approximately 50% polymer proportion, further components: mineral oil (INCI name: Mineral Oil) and tridecylpolyoxypropylenepolyoxyethylene ether (INCI name: PPG-1-Trideceth-6)) and Salcare® SC 96 (approximately 50% polymer proportion, further components: mixture of diesters of propylene glycol with a mixture of caprylic and capric acid (INCI name: Propylene Glycol Dicaprylate/Dicaprate) and tridecylpolyoxypropylenepolyoxyethylene ether (INCI name: PPG-1-Trideceth-6)).

Copolymers having monomer units according to formula (G1-I) preferably contain, acrylamide, methacrylamide, acrylic acid $C_{1-4}$ alkyl esters, and methacrylic acid $C_{1-4}$ alkyl esters as nonionogenic monomer units. Of these nonionogenic monomers, acrylamide is particularly preferred. These copolymers as well, as in the case of the homopolymers described above, can be crosslinked. A copolymer preferred according to the present invention is the crosslinked copolymer of acrylamide and methacryloyloxyethyltrimethylammonium chloride. Such copolymers, in which the monomers are present at a weight ratio of approximately 20:80, are commercially obtainable, as an approx. 50% nonaqueous polymer dispersion, under the designation Salcare® SC 92.

Additional preferred cationic polymers are, for example:

quaternized cellulose derivatives such as those obtainable commercially under the designations Celquat® and Polymer JR®. The compounds Celquat® H 100, Celquat® L 200, and Polymer JR®400 are preferred quaternized cellulose derivatives;

cationic alkylpolyglycosides according to DE Patent 44 13 686;

cationized honey, for example, the commercial product Honeyquat® 50;

cationic guar derivatives such as, in particular, the products marketed under the trade names Cosmedia® Guar and Jaguar®;

polysiloxanes having quaternary groups, such as, for example, the commercially obtainable products Q2-7224 (manufacturer: Dow Corning; a stabilized trimethylsilylamodimethicone), Dow Corning® 929 Emulsion (containing a hydroxylamino-modified silicone that is also referred to as amodimethicone), SM-2059 (manufacturer: General Electric), SLM-55067 (manufacturer: Wacker), and Abil®-Quat 3270 and 3272 (manufacturer: Th. Goldschmid; diquaternary polydimethylsiloxanes, Quaternium-80);

polymeric dimethyldiallylammonium salts and their copolymers with esters and amides of acrylic acid and methacrylic acid. The products available commercially under the designations Merquat® 100 (poly(dimethyldiallylammonium chloride)) and Merquat® 550 (dimethyldiallylammonium chloride/acrylamide copolymer) are examples of such cationic polymers;

copolymers of vinylpyrrolidone with quaternized derivatives of dialkylaminoalkylacrylate and -methacrylate, such as, for example, vinylpyrrolidone/dimethylaminoethylmethacrylate copolymers quaternized with diethylsulfate. Such compounds are obtainable commercially under the designations Gafquat® 734 and Gafquat® 755;

vinylpyrrolidone/vinylimidazolium methochloride copolymers, such as those offered under the designations Luviquat® FC 370, FC 550, FC 905, and HM 552;

quaternized poly(vinylalcohol); and the polymers known under the designations Polyquaternium 2, Polyquaternium 17, Polyquaternium-18, and Polyquaternium 27, having quaternary nitrogen atoms in the main polymer chain.

The polymers known under the designations Polyquaternium-24 (commercial product, e.g., Quatrisoft® LM 200) can similarly be used as cationic polymers. Likewise usable according to the present invention are the copolymers of vinylpyrrolidone such as those available as the commercial products Copolymer 845 (manufacturer: ISP), Gaffix® VC 713 (manufacturer: ISP), Gafquat® ASCP 1011, Gafquat® HS 110, Luviquat® 8155, and Luviquat® MS 370.

Additional cationic polymers usable according to the present invention are the so-called "temporarily cationic" polymers. These polymers usually contain an amino group that, at certain pH values, is present as a quaternary ammonium group and therefore cationically. Chitosan and its derivatives, such as those readily available commercially, for example, under the commercial designations Hydagen® CMF, Hydagen® HCMF, Kytamer® PC, and Chitolam® NB/101, are, for example, preferred.

Cationic polymers that are preferred for use according to the present invention are cationic cellulose derivatives and chitosan and its derivatives, in particular, the commercial products Polymer® JR 400, Hydagen® HCMF, and Kytamer® PC, cationic guar derivatives, cationic honey derivatives, in particular the commercial product Honeyquat® 50, cationic alkylpolyglycosides according to DE Patent 44 13 686, and polymers of the Polyquaternium-37 type.

Also to be listed among the cationic polymers are cationized protein hydrolysates, in which context the underlying protein hydrolysate can derive from animals, for example, from collagen, milk, or keratin, or from plants, for example, from wheat, corn, rice, potatoes, soy, or almonds, from marine life forms, for example, from fish collagen or algae, or biotechnologically obtained protein hydrolysates. The protein hydrolysates serving as the basis for the cationic derivatives usable according to the present invention can be obtained from the corresponding proteins by way of a chemical, in particular, alkaline or acid, hydrolysis, by an enzymatic hydrolysis, and/or a combination of both types of hydrolysis. The hydrolysis of proteins results, as a rule, in a protein hydrolysate having a molecular weight distribution from approximately 100 dalton up to several thousand dalton. Those cationic protein hydrolysates whose underlying protein component has a molecular weight from 100 to 25,000 dalton, preferably 250 to 5,000 dalton, are preferred. Also to be understood as cationic protein hydrolysates are quaternized amino acids and their mixtures. Quaternization of protein hydrolysates or of amino acids is often carried out by means of quaternary ammonium salts such as, for example, N,N-dimethyl-N-(n-alkyl)-N-(2-hydroxy-3-chloro-n-propyl)ammonium halides. The cationic protein hydrolysates can furthermore also be further derivatized. Typical examples that may be mentioned of cationic protein hydrolysates and derivatives are the following products listed under the INCI names in the "International Cosmetic Ingredient Dictionary and Handbook", (Seventh edition 1997, The Cosmetic, Toiletry, and Fragrance Association, 1101 17th Street, N.W., Suite 300, Washington, D.C. 20036-4702), and available commercially: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

The plant-based cationic protein hydrolysates and derivatives are very particularly preferred.

Further conditioning polymers usable according to the present invention are the amphoteric compounds recited in GB Unexamined Application 2 104 091, EP Unexamined Application 47 714, EP Unexamined Application 217 274, EP Unexamined Application 283 817, and DE Unexamined Application 28 17 369.

Amphoteric polymers used in preferred fashion are those polymerizates made up substantially of (a) Monomers having quaternary ammonium groups of the general formula (II)

$$R^1—CH=CR^2—CO-Z-(C_nH_{2n})—N^{(+)}R^3R^4R^5A^{(-)} \qquad (II)$$

in which $R^1$ and $R^2$, independently of one another, denote hydrogen or a methyl group, and $R^3$, $R^4$ and $R^5$, each independently of one another, denote an alkyl group having 1 to 4 carbon atoms, Z denotes an NH group or an oxygen atom, n is a whole number from 2 to 5, and $A^{(-)}$ is the anion of an organic or inorganic acid; and (b) monomeric carboxylic acids of the general formula (III)

$$R^6—CH=CR^7—COOH \qquad (III)$$

in which $R^6$ and $R^7$, independently of one another, denote hydrogen or a methyl group.

These compounds can be used according to the present invention both directly and in the form of salts that are obtained by neutralization of the polymerizates, for example, using an alkaline hydroxide. Regarding the details of manufacture of these polymerizates, reference is expressly made to the content of DE Unexamined Application 39 29 973. Those polymerizates in which monomers of type (a) are used in which $R^3$, $R^4$, and $R^5$ are methyl groups, Z is an NH group, and $A^{(-)}$ is a halide, methoxysulfate, or ethoxysulfate ion, are very particularly preferred; acrylamidopropyltrimethylammonium chloride is a particularly preferred monomer (a). Acrylic acid is preferably used as monomer (b) for the aforesaid polymerizates.

The two-component agents according to the present invention contain the conditioning polymers, preferably in a quantity from 0.01 to 5 wt %, in particular, in a quantity from 0.1 to 2 wt %, in each case based on the entire application preparation.

In the context of a third preferred embodiment, the two-component agents according to the present invention contain at least one UV filter. The UV filters suitable according to the present invention are not subject to any general restrictions in terms of their structure or physical properties. Instead, all UV filters usable in the cosmetics sector whose absorption maxima lie in the UVA (315-400 nm) UVB (280-315 nm), or UVC (<280 nm) regions are suitable. UV filters having an absorption maximum in the UVB region, in particular, in the region from approximately 280 to approximately 300 nm, are particularly preferred.

The UV filters preferred according to the present invention can be selected, for example, from substituted benzophenones, p-aminobenzoic acid esters, diphenylacrylic acid esters, cinnamic acid esters, salicylic acid esters, benzimidazoles, and o-aminobenzoic acid esters.

Examples of UV filters usable according to the present invention are 4-aminobenzoic acid, N,N,N-trimethyl-4-(2-oxoborn-3-ylidene methyl)aniline methylsulfate, 3,3,5-trimethylcyclohexylsalicylate (Homosalate), 2-hydroxy-4-methoxybenzophenone (Benzophenone-3; Uvinul® M 40, Uvasorb® MET, Neo Heliopan® BB, Eusolex® 4360), 2-phenylbenzimidazole-5-sulfonic acid and its potassium, sodium, and triethanolamine salts (phenylbenzimidazole-sulfonic acid; Parsol® HS; Neo Heliopan® Hydro), 3,3'-(1,4-phenylenedimethylene)-bis(7,7-dimethyl-2-oxo-bicyclo-[2.2.1]hept-1-yl-methanesulfonic acid) and its salts, 1-(4-tert.-butylphenyl)-3-(4-methoxyphenyl)-propane-1,3-dione (butyl methoxydibenzoylmethane; Parsol® 1789, Eusolex® 9020), α-(2-oxoborn-3-ylidene)toluene-4-sulfonic acid and its salts, ethoxylated 4-aminobenzoic acid ethyl ester (PEG-25 PABA; Uvinul® P 25), 4-dimethylaminobenzoic acid 2-ethylhexyl ester (Octyl Dimethyl PABA; Uvasorb® DMO, Escalol® 507, Eusolex® 6007), salicylic acid 2-ethylhexyl ester (Octyl Salicylate; Escalol® 587, Neo Heliopan® OS, Uvinul® O18), 4-methoxycinnamic acid isopentyl ester (Isoamyl p-Methoxycinnamate; Neo Heliopan® E 1000), 4-methoxycinnamic acid 2-ethylhexyl ester (Octyl Methoxycinnamate; Parsol® MCX, Escalol® 557, Neo Heliopan® AV), 2-hydroxy-4-methoxybenzophenone-5-sulfonic acid and its sodium salt (Benzophenone-4; Uvinul® MS 40; Uvasorb® S 5), 3-(4'-methylbenzylidene) D,L-camphor (4-methylbenzylidene camphor; Parsol® 5000, Eusolex® 6300), 3-benzylidene camphor (3-Benzylidene Camphor), 4-isopropylbenzylsalicylate, 2,4,6-trianilino-(p-carbo-2'-ethylhexyl-1'-oxi)-1,3,5-triazine, 3-imidazol-4-ylacrylic acid and its ethyl esters, polymers of N-{(2 and 4)-[2-oxoborn-3-ylidenemethyl]benzyl}acrylamide, 2,4-dihydroxybenzophenone (Benzophenone-1; Uvasorb® 20 H, Uvinul® 400), 1,1'-diphenylacrylonitrilic acid 2-ethylhexyl ester (Octocrylene; Eusolex® OCR, Neo Heliopan® Type 303, Uvinul® N 539 SG), o-aminobenzoic acid menthyl ester (Menthyl Anthranilate; Neo Heliopan® MA), 2,2',4,4'-tetrahydroxybenzophenone (Benzophenone-2; Uvinul® D-50), 2,2'-dihydroxy-4,4'-dimethoxybenzophenone (Benzophenone-6), 2,2'-dihydroxy-4,4'-dimethoxybenzophenone-5-sodiumsulfonate, and 2-cyano-3,3-diphenylacrylic acid 2'-ethylhexyl ester. 4-aminobenzoic acid, N,N,N-trimethyl-4-(2-oxoborn-3-ylidene methyl)aniline methylsulfate, 3,3,5-trimethylcyclohexylsalicylate, 2-hydroxy-4-methoxybenzophenone, 2-phenylbenzimidazole-5-sulfonic acid its potassium, sodium, and triethanolamine salts, 3,3'-(1,4-phenylenedimethylene)-bis(7,7-dimethyl-2-oxo-bicyclo-[2.2.1] hept-1-ylmethanesulfonic acid) and its salts, 1-(4-tert.-butylphenyl)-3-(4-methoxyphenyl)propane-1,3-dione, α-(2-oxoborn-3-ylidene)toluene-4-sulfonic acid and its salts, ethoxylated 4-aminobenzoic acid ethyl ester, 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and its sodium salt, 3-(4'-methyl-benzylidene)-D,L-camphor, 3-benzylidene camphor, 4-isopropylbenzyl salicylate, 2,4,6-tri-anilino-(p-carbo-2'-ethylhexyl-1'-oxi)-1,3,5-triazine, 3-imidazol-4-ylacrylic acid and its ethyl esters, and polymers of N-{(2 and 4)-[2-oxoborn-3-ylidenemethyl]benzyl}acrylamide are preferred. Very particularly preferred according to the present invention are 2-hydroxy-4-methoxy-benzophenone, 2-phenylbenzimidazole-5-sulfonic acid and its potassium, sodium, and triethanolamine salts, 1-(4-tert.-butylphenyl)-3-(4-methoxyphenyl)propane-1,3-dione, 4-methoxycinnamic acid 2-ethylhexyl ester, and 3-(4'-methylbenzylidene) D,L camphor.

Those UV filters whose molar extinction coefficient at the absorption maximum is above 15,000, in particular, above 20,000, are preferred.

Moreover, it has been found that with structurally similar UV filters, in many cases the water-insoluble compound exhibits, in the context of the teaching of the present invention, the greater effectiveness as compared with water-soluble compounds of this kind that differ from it by having one or more additionally ionic groups. In the context of the invention, those UV filters of which no more than 1 wt %, in particular, no more than 0.1 wt %, dissolves in water at 20° C. are understood to be water-insoluble. Furthermore, these compounds should be soluble at a proportion of at least 0.1 wt %, in particular, at least 1 wt %, in common cosmetic oil components at room temperature. The use of water-insoluble UV filters can, therefore, be preferred according to the present invention.

According to a further embodiment of the present invention, those UV filters that comprise a cationic group, in particular, a quaternary ammonium group, are preferred.

These UV filters exhibit the general structure U-Q.

The structural part U denotes a group that absorbs UV radiation. In principle, this group can be derived from the aforementioned known UV filters usable in the cosmetics sector, in which one group, generally a hydrogen atom, of the UV filter is replaced by a cationic group Q, in particular, by a quaternary amino function.

Compounds from which structural part U can be derived are, for example,
substituted benzophenones;
p-aminobenzoic acid esters;
diphenylacrylic acid esters;
cinnamic acid esters;
salicylic acid esters;
benzimidazoles; and
o-aminobenzoic acid esters.

Structural parts U that are derived from cinnamic acid amide or from N,N-dimethylaminobenzoic acid amide are preferred according to the present invention.

In principle, structural parts U can be selected so that the absorption maximum of the UV filters can lie both in the UVA (315-400 nm) region and in the UVB (280-315 nm) region, or in the UVC (<280 nm) region. UV filters having an absorption maximum in the UVB region, in particular, in the region from approximately 280 to approximately 300 nm, are particularly preferred.

Furthermore, structural part U is preferably selected, including as a function of structural part Q, in such a way that the molar extinction coefficient of the UV filter at the absorption maximum is above 15,000, in particular above 20,000.

Structural part Q preferably contains a quaternary ammonium group as a cationic group. In principle, this quaternary ammonium group can be bound directly to structural part U, so that structural part U represents one of the four substituents of the positively charged nitrogen atom. Preferably, however, one of the four substituents on the positively charged nitrogen atom is a group, in particular, an alkylene group having 2 to 6 carbon atoms, that functions as a connection between structural part U and the positively charged nitrogen atom.

Advantageously, the group Q has the general structure —$(CH_2)X$—$N^+R^1R^2R^3$ $X^-$, in which x denotes a whole number from 1 to 4, $R^1$ and $R^2$, independently of one another, denote $C_{1-4}$ alkyl groups, $R^3$ denotes a $C_{1-22}$ alkyl group or a benzyl group, and $X^-$ denotes a physiologically acceptable anion. In the context of this general structure, x preferably denotes the number 3, $R^1$ and $R^2$ each denote a methyl group, and $R^3$ denotes either a methyl group or a saturated or unsaturated, linear or branched hydrocarbon chain having 8 to 22, in particular, 10 to 18, carbon atoms.

Physiologically acceptable anions are, for example, inorganic anions such as halides, in particular, chloride, bromide and fluoride, sulfate ions, and phosphate ions, as well as organic anions such as lactate, citrate, acetate, tartrate, methosulfate, and tosylate.

Two preferred UV filters having cationic groups are the compounds cinnamic acid amidopropyltrimethylammonium chloride (Incroquat® UV-283), and dodecyldimethylaminobenzamidopropyldimethylammonium tosylate (Escalol® HP 610), available as commercial products.

The teaching of the present invention also encompasses the use of a combination of several UV filters. In the context of this embodiment, the combination of at least one water-insoluble UV filter with at least one UV filter having a cationic group is preferred.

The UV filters are contained in the agents according to the present invention, usually in quantities from 0.01-5 wt % based on the entire application preparation. Quantities from 0.1-2.5 wt % are preferred.

In the context of a fourth preferred embodiment, the two-component agents according to the present invention contain as a conditioning substance at least one vitamin, one provitamin, one vitamin precursor, and/or one of their derivatives.

Those vitamins, provitamins, and vitamin precursors that are usually assigned to groups A, B, C, E, F, and H are preferred according to the present invention.

The group of substances referred to as vitamin A includes retinol (vitamin A1) as well as 3,4-didehydroretinol (vitamin A2). β-carotene is the provitamin of retinol. Vitamin A components that are suitable according to the present invention are, for example, vitamin A acid and its esters, vitamin A aldehyde, and vitamin A alcohol as well as its esters such as the palmitate and acetate. The preparations used according to the present invention contain the vitamin A component, preferably in quantities from 0.05-1 wt % based on the entire application preparation.

Members of the vitamin B group or vitamin B complex are, among others:

Vitamin $B^1$ (thiamin)

Vitamin $B^2$ (riboflavin)

Vitamin $B^3$. The compounds nicotinic acid and nicotinic acid amide (niacinamide) are often listed under this designation. Nicotinic acid amide is preferred according to the present invention; it is contained in the agents according to the present invention preferably in quantities from 0.05 to 1 wt % based on the entire application preparation.

Vitamin $B^5$ (pantothenic acid, panthenol, and pantolactone). In the context of this group, panthenol and/or pantolactone are preferably used. Derivatives of panthenol usable according to the present invention are, in particular, the esters and ethers of panthenol as well as cationically derivatized panthenols. Individual representatives are, for example, panthenol triacetate, panthenol monoethyl ether and its monoacetate, and the cationic panthenol derivatives disclosed in WO 92/13829. The aforesaid compounds of the vitamin $B^5$ type are contained in the agents according to the present invention preferably in quantities from 0.05-10 wt % based on the entire application preparation. Quantities from 0.1-5 wt % are particularly preferred.

Vitamin $B^6$ (pyridoxine as well as pyridoxamine and pyridoxal). The aforesaid compounds of the vitamin $B^6$ type are contained in the agents according to the present invention preferably in quantities from 0.01-5 wt % based on the entire application preparation. Quantities from 0.05-1 wt % are particularly preferred.

Vitamin C (ascorbic acid). Vitamin C is utilized in the agents used according to the present invention, preferably in quantities from 0.1 to 3 wt % based on the entire application preparation. Utilization in the form of the palmitic acid ester, the glucosides or the phosphates can be preferred. Utilization in combination with tocopherols can likewise be preferred.

Vitamin E (tocopherols, in particular, α-tocopherol). Tocopherol and its derivatives, which include, in particular, the esters such as the acetate, the nicotinate, the phosphate, and the succinate, are contained in the agents according to the present invention, preferably in quantities from 0.05-1 wt % based on the entire application preparation.

Vitamin F. The term "vitamin F" is usually understood to mean essential fatty acids, in particular linoleic acid, linolenic acid, and arachidonic acid.

Vitamin H. This refers to (3aS,4S, 6aR)-2-oxohexahydrothienol[3,4-d]-imidazole-4-valeric acid, for which the common name "biotin" has nevertheless since become established. Biotin is contained in the agents according to the present invention preferably in quantities from 0.0001 to 1.0 wt %, in particular, in quantities from 0.001 to 0.01 wt %, in each case based on the entire application preparation.

The two-component agents according to the present invention preferably contain vitamins, provitamins, and vitamin precursors from groups A, B, C, E and H.

Panthenol, pantolactone, pyridoxine and its derivatives, as well as nicotinic acid amide and biotin, are particularly preferred.

In the context of a fifth preferred embodiment, the two-component agents according to the present invention contain at least one plant extract.

These extracts are usually produced by the extraction of the whole plant. In individual cases, however, it may also be preferred to produce the extracts exclusively from blossoms and/or leaves of the plant.

With regard to the plant extracts usable according to the present invention, reference is made in particular to the extracts that are listed in the Table beginning on page 44 of the 3rd edition of the Guideline for declaring the contents of cosmetic agents [Leitfaden zur Inhaltsstoffdeklaration kosmetischer Mittel], published by the Association of the personal hygiene and washing agents industry [Industrieverband Körperpflege- und Waschmittel e.V. (IKW)], Frankfurt.

According to the present invention the extracts from green tea, oak bark, nettle, hamamelis, hops, henna, chamomile, burdock root, horsetail, hawthorn, linden blossom, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root are especially preferred.

Particularly preferred are the extracts from green tea, oak bark, nettle, hamamelis, hops, chamomile, burdock root, horsetail, linden blossom, almond, aloe vera, coconut, mango, apricot, lemon, wheat, kiwi fruit, melon, orange, grapefruit, salvia, rosemary, birch, lady's-smock, wild thyme, yarrow, restharrow, meristem, ginseng, and ginger root.

The extracts from green tea, almond, aloe vera, coconut, mango, apricot, lemon, wheat, kiwi fruit, and melon are very particularly preferred.

Water, alcohols, and mixtures thereof can be used as extraction agents for manufacturing the aforesaid plant extracts. Among the alcohols, lower alcohols such as ethanol and isopropanol, but in particular, polyvalent alcohols such as ethylene glycol and propylene glycol, both as sole extraction agents and mixed with water, are preferred. Plant extracts based on water/propylene glycol at a ratio from 1:10 to 10:1 have proven particularly suitable.

According to the present invention the plant extracts can be used in both pure and diluted form. If they are used in diluted form, they usually contain approximately 2 to 80 wt % active substance, and contain, as the solvent, the extraction agent or extraction agent mixture used to obtain them.

Furthermore, it can be preferred to use in the compositions according to the present invention mixtures of several, in particular two, different plant extracts.

In the context of a sixth embodiment, the two-component agents according to the present invention contain as a conditioning substance at least one carboxylic acid.

Short-chain carboxylic acids can be particularly advantageous for purposes of the invention. Short-chain carboxylic acids and their derivatives are understood, for purposes of the invention, to be carboxylic acids that can be saturated or unsaturated and/or straight-chain or branched or cyclic and/or aromatic and/or heterocyclic, and have a molecular weight below 750. Saturated or unsaturated straight-chain or branched carboxylic acids having a chain length of 1 to 16 C atoms in the chain can be preferred for purposes of the invention; those having a chain length of 1 to 12 C atoms in the chain are very particularly preferred.

The short-chain carboxylic acids for purposes of the invention can comprise one, two, three, or more carboxy groups. Carboxylic acids having multiple carboxy groups, in particular di- and tricarboxylic acids, are preferred for purposes of the invention. The carboxy groups can be present entirely or partly as an ester, acid anhydride, lactone, amide, imidic acid, lactam, lactim, dicarboximide, carbohydrazide, hydrazone, hydroxam, hydroxime, amidine, amide oxime, nitrile, phosphonic or phosphate ester. Of course the carboxylic acids according to the present invention can be substituted along the carbon chain or the ring structure. Among the substituents of the carboxylic acids usable according to the present invention may be listed, for example, $C_1$-$C_8$ alkyl, $C_2$-$C_8$ alkenyl, aryl, aralkyl and aralkenyl, hydroxymethyl, $C_2$-$C_8$ hydroxyalkyl, $C_2$-$C_8$ hydroxyalkenyl, aminomethyl, $C_2$-$C_8$ aminoalkyl, cyano, formyl, oxo, thioxo, hydroxy, mercapto, amino, carboxy or imino groups. Preferred substituents are $C_1$-$C_8$ alkyl, hydroxymethyl, hydroxy, amino and carboxy groups. Substituents in the α- position are particularly preferred. Very particularly preferred substituents are hydroxy, alkoxy, and amino groups, in which context the amino function can be further substituted, if applicable, with alkyl, aryl, aralkyl, and/or alkenyl radicals. Furthermore, the phosphonic and phosphate esters are likewise preferred carboxylic acid derivatives.

The following may be mentioned as examples of carboxylic acids usable according to the present invention: formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-napthalenepentaacetic acid, malonaldehydic acid, 4-hydroxyphthalamidic acid, 1-pyrazolecarboxylic acid, gallic acid, or propanetricarboxylic acid, a dicarboxylic acid selected from the group formed by compounds of the general formula (N-I):

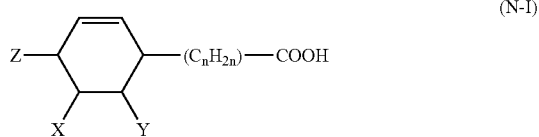

in which Z denotes a linear or branched alkyl or alkenyl group having 4 to 12 carbon atoms, n a number from 4 to 12, and one of the two groups X and Y denotes a COOH group and the other hydrogen or a methyl or ethyl radical, dicarboxylic acids of the general formula (N-I) that additionally bear 1 to 3 methyl or ethyl substituents on the cyclohexene ring, as well as dicarboxylic acids resulting from the dicarboxylic acids according to formula (N-I), in formal terms, by the attachment of one molecule of water to the double bond in the cyclohexene ring.

Dicarboxylic acids of the formula (N-I) are known in the literature. A manufacturing method may be inferred, for example, from U.S. Pat. No. 3,753,968.

The dicarboxylic acids of formula (N-I) can be produced, for example, by reacting multiply unsaturated dicarboxylic acids with unsaturated monocarboxylic acids in the form of a Diels-Alder cyclization. It is usual to proceed from a multiply unsaturated fatty acid as a dicarboxylic acid component. Linoleic acid, accessible from natural fats and oils, is preferred. Acrylic acid, in particular, but also, e.g., methacrylic acid and crotonic acid, is preferred as a monocarboxylic acid component. Diels-Alder reactions usually result in isomer mixtures in which one component is present in excess. Both these isomer mixtures and the pure compounds can be used according to the present invention.

Also usable in addition to the preferred dicarboxylic acids according to formula (N-I) are those dicarboxylic acids that differ from the compounds according to formula (N-I) by having 1 to 3 methyl or ethyl substituents on the cyclohexyl ring, or are formed from those compounds, in formal terms, by the attachment of one molecule of water to the double bond of the cyclohexene ring.

The dicarboxylic acid (mixture) resulting from the reaction of linoleic acid with acrylic acid has proven to be particularly effective according to the present invention. This is a mixture of 5- and 6-carboxy-4-hexyl-2-cyclohexene-1-octanoic acids. Such compounds are commercially available under the designations Westvaco Diacid® 1550 and Westvaco Diacid® 1595 (manufacturer: Westvaco).

In addition to the short-chain carboxylic acids according to the present invention listed above by way of example, their physiologically acceptable salts can also be used according to the present invention. Examples of such salts are the alkali, alkaline-earth, and zinc salts, as well as ammonium salts, among which the mono-, di-, and trimethyl-, ethyl-, and hydroxyethylammonium salts are also to be understood in the context of the present Application. In very particularly preferred fashion, however, acids neutralized with alkaline-reacting amino acids, for example, arginine, lysine, ornithine, and histidine can be used in the context of the invention. It can also be preferred for formulation reasons to select the carboxylic acid from the water-soluble representative, in particular, the water-soluble salts.

It is furthermore preferred according to the present invention to utilize 2-pyrrolidinone-5-carboxylic acid and its derivatives as a carboxylic acid. Particularly preferred are the sodium, potassium, calcium, magnesium or ammonium salts, in which context the ammonium ion carries, in addition to hydrogen, one to three $C_1$-$C_4$ alkyl groups. The sodium salt is very particularly preferred. The quantities used in the agents according to the present invention are preferably 0.05 to 10 wt % based on the entire application preparation, particularly preferably, 0.1 to 5 wt %, and especially preferably, 0.1 to 3 wt %.

It is further preferred according to the present invention to use hydroxycarboxylic acids, and in this context in turn, in particular, the dihydroxy-, trihydroxy- and polyhydroxycarboxylic acids, as well as the dihydroxy, trihydroxy- and polyhydroxydi, tri- and polycarboxylic acid. In this context, it has been found that in addition to the hydroxycarboxylic acids, the hydroxycarboxylic acid esters, as well as mixtures of hydroxycarboxylic acids and their esters, and also polymeric hydroxycarboxylic acids and their esters, can be very particularly preferred. Preferred hydroxycarboxylic acid esters are, for example, full esters of glycolic acid, lactic acid, malic acid, tartaric acid, or citric acid. Additional hydroxycarboxylic acid esters that are suitable in principle are esters of β-β-hydroxypropionic acid, of tartronic acid, of D-gluconic acid, of saccharic acid, of mucic acid, or of glucuronic acid. Suitable as alcohol components of these esters are primary, linear or branched aliphatic alcohols having 8-22 C atoms, i.e., for example, fatty alcohols or synthetic fatty alcohols. The esters of $C_{12}$-$C_{15}$ fatty alcohols are particularly preferred in this context. Esters of this type are obtainable commercially, e.g., under the trademark Cosmacol® of EniChem, Augusta Industriale. Particularly preferred polyhydroxypolycarboxylic acids are polylactic acid und polytartaric acid as well as their esters.

In the context of a seventh preferred embodiment, the two-component agents according to the present invention contain as a conditioning substance at least one protein hydrolysate and/or one of its derivatives.

Protein hydrolysates are product mixtures obtained by the acid-, base-, or enzyme-catalyzed breakdown of proteins. The term "protein hydrolysates" is also understood according to the present invention to mean total hydrolysates, as well as individual amino acids and their derivatives, as well as mixtures of different amino acids. Polymers constructed from amino acids and amino-acid derivatives are also to be understood under the term "protein hydrolysates" according to the present invention. Included among the latter are, for example, polyalanine, polyasparagine, polyserine, etc. Further examples of compounds usable according to the present invention are L-alanyl-L-proline, polyglycine, glycyl-L-glutamine, or D/L-methionine-S-methylsulfonium chloride. β-amino acids and their derivatives, such as β-alanine, anthranilic acid, or hippuric acid, can of course also be used according to the present invention. The molecular weight of the protein hydrolysates usable according to the present invention is between 75 (the molecular weight of glycine) and 200,000; preferably the molecular weight is 75 to 50,000 dalton, and in very particularly preferred fashion 75 to 20,000 dalton.

According to the present invention, protein hydrolysates of both plant and animal origin, or of marine or synthetic origin, can be used.

Animal protein hydrolysates are, for example, elastin, collagen, keratin, silk, and milk protein hydrolysates, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm), and Kerasol® (Croda).

The use of protein hydrolysates of plant origin, e.g., soy-, almond-, bean-, potato-, and wheat-protein hydrolysates, is preferred according to the present invention. Such products are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), and Crotein® (Croda).

Although the use of protein hydrolysates as such is preferred, it is also optionally possible to use, in place of them, amino-acid mixtures obtained in different fashion. It is likewise possible to use derivatives of protein hydrolysates, for example, in the form of their fatty acid condensation products. Such products are marketed, for example, under the designations Lamepon® (Cognis), Lexein® (Inolex), Crolastin® (Croda), Crosilk® (Croda), or Crotein® (Croda).

The teaching according to the present invention of course encompasses all isomeric forms, such as cis-trans isomers, diastereomers, and chiral isomers.

It is also possible according to the present invention to utilize a mixture of several protein hydrolysates.

The protein hydrolysates are contained in the two-component agents according to the present invention, for example, in concentrations from 0.01 wt % to 20 wt %, preferably from 0.05 wt % to 15 wt %, and very particularly preferably, in quantities from 0.05 wt % to 5 wt %, in each case based on the entire application preparation.

In the context of an eighth preferred embodiment, the preparations according to the present invention contain as a conditioning substance ectoin or ectoin derivatives, allantoin, taurine, and/or bisabolol.

The terms "ectoin and ectoin derivatives" are understood, according to the present invention, to mean compounds of formula (IV):

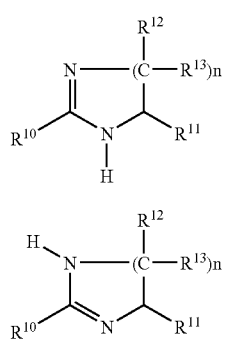

(IVa)

(IVb)

and/or their physiologically acceptable salts and/or an isomeric or stereoisomeric form, in which $R^{10}$ denotes a hydrogen atom, a branched or unbranched $C_1$-$C_4$ alkyl radical, or a $C_2$-$C_4$ hydroxyalkyl radical;

$R^{11}$ denotes a hydrogen atom, a —COOR$^{14}$ grouping, or a —CO(NH)R$^{14}$ grouping, in which context R$^{14}$ can denote a $C_1$-$C_4$ alkyl radical, an amino acid radical, or a dipeptide or tripeptide radical;

$R^{12}$ and $R^{13}$ denote, independently of one another, a hydrogen atom, a $C_1$-$C_4$ alkyl radical, or a hydroxy group, with the stipulation that the two radicals must not simultaneously denote a hydroxy group; and n denotes a whole number from 1 to 3.

Suitable physiologically acceptable salts of the general compounds according to formula (IVa) or (IVb) are, for example, the alkaline, alkaline-earth, ammonium, triethylamine, or tris-(2-hydroxyethyl)amine salts, as well as those that result from the reaction of compounds according to formula (IVa) or (IVb) with inorganic and organic acids such as hydrochloric acid, phosphoric acid, sulfuric acid, branched or unbranched, substituted or unsubstituted (for example, with one or more hydroxy groups) $C_1$-$C_4$ mono- or dicarboxylic acids, aromatic carboxylic acids and sulfonic acids such as acetic acid, citric acid, benzoic acid, maleic acid, fumaric acid, tartaric acid, and p-toluenesulfonic acid. Examples of particularly preferred physiologically acceptable salts are the Na, K, Mg, Ca, and ammonium salts of the compounds according to formula (IVa) or (IVb), as well as the salts that result from the reaction of compounds according to formula (IVa) or (IVb) with hydrochloric acid, acetic acid, citric acid, and benzoic acid.

Isomeric or stereoisomeric forms of the compounds according to formula (IVa) or (IVb) are understood, according to the present invention, to mean all optical isomers, diastereomers, racemates, zwitterions, cations, or mixtures thereof that occur.

The term "amino acid" is understood to mean the stereoisomeric forms, e.g., D- and L- forms, of the following compounds:

asparagine, arginine, asparagic acid, glutamine, glutamic acid, β-alanine, γ-aminobutyrate, $N_\epsilon$-acetyllysine, $N_{67}$-acetylornithine, $N_\gamma$-acetyldiaminobutyrate, $N_\alpha$-acetyldiaminobutyrate, histidine, isoleucine, leucine, methionine, phenylalanine, serine, threonine and tyrosine. L-amino acids are preferred. Amino-acid radicals are derived from the corresponding amino acids. The following amino-acid radicals are preferred:

Gly, Ala, Ser, Thr, Val, β-Ala, γ-aminobutyrate, Asp, Glu, Asn, Aln, Nε-acetyllysine, $N_\delta$-acetylornithine, Nγ-acetyldiaminobutyrate, Nα-acetyldiaminobutyrate.

The amino acids have been abbreviated in accordance with customary notation. The di- or tripeptide radicals are acid amides in terms of their chemical nature, and decompose upon hydrolysis into two or three amino acids. The amino acids in the di- or tripeptide radical are joined to one another by amide bonds.

With regard to the manufacture of di- and tripeptide radicals, reference is expressly made to EP 0 671 161 A1 of the Marbert company. Examples of di- and tripeptide radicals may also be inferred from the disclosure of EP 0 671 161 A1.

Examples of $C_1$-$C_4$ alkyl groups in the compounds according to the present invention are methyl, ethyl, n-propyl, isopropyl, n-butyl, isobutyl and tert.-butyl. Preferred alkyl groups are methyl and ethyl; methyl is a particularly preferred alkyl group. Preferred $C_2$-$C_4$ hydroxyalkyl groups are the 2-hydroxyethyl, 3-hydroxypropyl or 4-hydroxybutyl groups; 2-hydroxyethyl is a particularly preferred hydroxyalkyl group.

The two-component agents according to the present invention contain these conditioning substances preferably in quantities from 0.001 to 2, in particular, from 0.01 to 0.5 wt %, in each case based on the entire application preparation.

In the context of a ninth preferred embodiment, preparation (B) contains at least one mono- or oligosaccharide as a conditioning substance.

Both monosaccharides and oligosaccharides, for example, raw sugar, milk sugar, and raffinose, can be used. The use of monosaccharides is preferred according to the present invention. Among the monosaccharides, those compounds containing 5 or 6 carbon atoms are in turn preferred.

Suitable pentoses and hexoses are, for example, ribose, arabinose, xylose, lyxose, allose, altrose, glucose, mannose, gulose, idose, galactose, talose, fucose and fructose. Arabinose, glucose, galactose and fructose are carbohydrates that are preferably used; it is very particularly preferred to use glucose, which is suitable both in the D-(+) or L-(−) configuration or as a racemate.

Derivatives of these pentoses and hexoses, such as the corresponding -onic and -uronic acids (sugar acids), sugar alcohols, and glycosides, can also be used according to the present invention. Preferred sugar acids are gluconic acid, glucuronic acid, saccharic acid, mannosaccharic acid, and mucic acid. Preferred sugar alcohols are sorbitol, mannitol, and dulcitol. Preferred glycosides are the methylglucosides.

Because the mono- or oligosaccharides that are used are usually obtained from natural raw materials such as starch, in general they exhibit the configurations corresponding to those raw materials (e.g., D-glucose, D-fructose and D-galactose).

The mono- or oligosaccharides are contained in the hair treatment agents according to the present invention, preferably in a quantity from 0.1 to 8 wt %, in particularly preferred fashion, from 1 to 5 wt %, based on the entire application preparation.

In the context of a tenth embodiment, preparation (B) contains at least one silicone oil and/or one silicone gum as a conditioning substance.

Silicones or silicone gums suitable according to the present invention are, in particular, dialkyl- and alkylarylsiloxanes such as, for example, dimethylpolysiloxane and methylphenylpolysiloxane, as well as their alkoxylated, quaternized, or even anionic derivatives.

Examples of such silicones are:
- oligomeric polydimethylcyclosiloxanes (INCI name: Cyclomethicone), in particular, the tetrameric and pentameric compounds, which are marketed by Dow Corning as commercial products DC 344 and DC 345, respectively;
- hexamethyldisiloxane (INCI name: Hexamethyldisiloxane), e.g., the product marketed under the designation Abil® K 520;
- polymeric polydimethylsiloxanes (INCI name: Dimethicone), e.g., the products marketed by Dow Corning under the designation DC 200;
- polyphenylmethylsiloxanes (INCI name: Phenyl Trimethicone), e.g., the commercial product DC 556 Fluid of Dow Corning;
- silicone-glycol copolymers (INCI name: Dimethicone Copolyol), e.g., the commercial products DC 190 and DC 193 of Dow Corning;
- esters and partial esters of the silicone-glycol copolymers, such as those marketed, for example, by the Fanning company under the commercial designation Fancorsil® LIM (INCI name: Dimethicone Copolyol Meadowfoamate);
- dimethylsiloxanes having hydroxy end caps (INCI name: Dimethiconol), e.g., the commercial products DC 1401 and Q2-1403 of Dow Corning;
- aminofunctional polydimethylsiloxanes and hydroxylamino-modified silicones (INCI names including Amodimethicone and Quaternium-80), such as the commercial products XF42-B1989 (manufacturer: GE Toshiba Silicones) Q2-7224 (manufacturer: Dow Corning; a stabilized trimethylsilylamodimethicone), Dow Corning® 939 Emulsion (containing a hydroxylamino-modified silicone that is also referred to as amodimethicone), SM-2059 (manufacturer: General Electric), SLM-55067 (manufacturer: Wacker), and Abil®-Quat 3270 and 3272 (manufacturer: Th. Goldschmidt);
- anionic silicone oils such as, for example, the product Dow Corning® 1784;
- amino modified organosilicones such as, for example, the product Abil Soft A843 (manufacturer: Osi Specialties).

According to a preferred embodiment, the preparations according to the present invention contain a combination of a volatile and a non-volatile silicone. Those silicones that exhibit a volatility equal to or greater than the volatility of cyclic pentameric dimethylsiloxane are volatile for purposes of the invention. Such combinations are also available as commercial products (e.g., Dow Corning® 1401, Dow Corning® 1403, and Dow Corning® 1501, in each case mixtures of a cyclomethicone and a dimethiconol).

According to a particularly preferred embodiment, preparation (B) contains as a conditioning substance a dialkylpolysiloxane or one of its derivatives. The alkyl groups methyl, ethyl, i-propyl, and n-propyl are preferred. Dimethylpolysiloxane or one of its derivatives is particularly preferred for use. The derivatives of dimethylpolysiloxane that are aminofunctional are preferred. A very particularly preferred derivative is commercially obtainable under the INCI name Amodimethicone.

The preparations according to the present invention contain the silicones, preferably in quantities from 0.01-10 wt %, in particular, 0.1-5 wt %, based on the entire application preparation.

In the context of an eleventh embodiment, preparation (B) contains at least one lipid as a conditioning substance.

Lipids suitable according to the present invention are phospholipids, for example, soy lecithin, egg lecithin, and kephalins, as well as the substances known by the INCI names Linoleamidopropyl PG-Dimonium Chloride Phosphate, Cocamidopropyl PG-Dimonium Chloride Phosphate, and Stearamidopropyl PG-Dimonium Chloride Phosphate. These are marketed, for example, by the Mona company under the commercial designations Phospholipid EFA®, Phospholipid PTC®, and Phospholipid SV®.

The preparations according to the present invention contain the lipids, preferably in quantities from 0.01-10 wt %, in particular, 0.1-5 wt % based on the entire application preparation.

In the context of a twelfth embodiment, preparation (B) contains at least one oily substance as a conditioning substance.

Among the natural and synthetic cosmetic oily substances may be listed, for example:
- Vegetable oils. Examples of such oils are sunflower oil, olive oil, soybean oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 C atoms, in particular, 12 to 24 C atoms, such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as ditert.-butyl ether, diisopentyl ether, di-3-ethyldecyl ether, tert.-butyl-n-octyl ether, isopentyl-n-octyl ether, and 2-methylpentyl-n-octyl ether. The compounds 1,3-di-(2-ethylhexyl) cyclohexane (Cetiol® S) and di-n-octyl ether (Cetiol® OE), available as commercial products, can be preferred.

Ester oils. "Ester oils" are to be understood as the esters of $C_6$-$C_{30}$ fatty acids with $C_2$-$C_{30}$ fatty alcohols. The monoesters of fatty acids with alcohols having 2 to 24 C atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid, and erucic acid, as well as industrial mixtures thereof that occur, for example, upon high-pressure cleavage of natural fats and oils, upon oxidation of aldehydes from Roelen oxosynthesis, or upon dimerization of unsaturated fatty acids. Examples of the fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of industrial methyl esters based on fats and oils or aldehydes from Roelen oxosynthesis, and as a monomer fraction upon dimerization of unsaturated fatty alcohols. Particularly preferred according to the present invention are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), Oleyl Oleate (Cetiol®), lauric acid hexyl ester (Cetiol® A), di-n-butyl adipate (Cetiol® B), myristyl myristate (Cetiol® MM), Cetearyl Isononanoate (Cetiol® SN), oleic acid decyl ester (Cetiol® V).

Dicarboxylic acid esters such as di-n-butyl adipate, di(2-ethylhexyl) adipate, di(2-ethylhexyl) succinate, and diisotridecyl acelaate, as well as diol esters such as ethylene glycol dioleate, ethylene glycol diisotridecanoate, propylene glycol di(2-ethyl hexanoate), propylene glycol diisostearate, propylene glycol dipelargonate, butanediol diisostearate, neopentyl glycol dicaprylate.

Symmetrical, asymmetrical, or cyclic esters of carbonic acid with fatty alcohols, described, for example, in DE Unexamined Application 197 56 454, glycerol carbonate, or dicaprylyl carbonate (Cetiol® CC).

Fatty acid triesters of saturated and/or unsaturated linear and/or branched fatty acids with glycerol.

Fatty acid partial glycerides, which are to be understood as monoglycerides, diglycerides, and industrial mixtures thereof. When industrial products are used, small quantities of triglycerides can still be present for manufacturing-related reasons. The partial glycerides preferably conform to formula (D4-I):

in which $R^1$, $R^2$ and $R^3$, independently of one another, denote hydrogen or a linear or branched, saturated and/or unsaturated acyl radical having 6 to 22, preferably 12 to 18, carbon atoms, with the stipulation that at least one of these groups denotes an acyl radical and at least one of these groups denotes hydrogen. The sum (m+n+q) denotes 0 or numbers from 1 to 100, preferably 0 or 5 to 25. $R^1$ preferably denotes an acyl radical and $R^2$ and $R^3$ denote hydrogen, and the sum (m+n+q) is 0. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachidic acid, gadoleic acid, behenic acid and erucic acid, as well as industrial mixtures thereof. Oleic acid monoglycerides are preferably used.

The quantity of the natural and synthetic cosmetic oily substances used in the two-component agents according to the present invention is usually 0.1-30 wt % based on the entire application preparation, preferably 0.1-20 wt %, and in particular, 0.1-15 wt %.

In the context of a thirteenth embodiment, preparation (B) contains an enzyme as a conditioning substance. Enzymes particularly preferred according to the present invention are selected from a group made up of proteases, lipases, transglutaminase, oxidases and peroxidases.

In the context of a fourteenth embodiment, the two-component agents according to the present invention contain at least one pearl extract.

Mussel pearls are made up substantially of inorganic and organic calcium salts, trace elements, and proteins. Pearls can easily be obtained from cultivated mussels. Mussel cultivation can be accomplished in both fresh water and seawater, which can have an effect on the constituents of the pearls. A pearl extract that derives from mussels cultivated in seawater or salt water is preferred according to the present invention. The pearls are made up largely of aragonite (calcium carbonate), conchiolin, and an albuminoid; the latter constituents are proteins. Also contained in pearls are magnesium and sodium salts, inorganic silicon compounds, and phosphates.

The pearls are powdered for production of the pearl extract. The powdered pearls are then extracted with the usual methods. Water, alcohols, and mixtures thereof can be used as extraction agents for production of the pearl extracts. "Water" is to be understood in this context as both demineralized water and seawater. Among the alcohols, lower alcohols such as ethanol and isopropanol, but in particular, polyvalent alcohols such as glycerol, diglycerol, triglycerol, polyglycerol, ethylene glycol, propylene glycol, and butylene glycol, both as a sole extraction agent and also mixed with demineralized water or seawater, are preferred. Pearl extracts based on water/glycerol mixtures have proven to be particularly suitable. Depending on the extraction conditions, the pearl proteins (conchiolin and albuminoid) can be present to a very large extent in the natural state, or already partly or very largely as protein hydrolysates. A pearl extract in which conchiolin and albuminoid are already present in partly hydrolyzed fashion is preferred. The essential amino acids of these proteins are glutamic acid, serine, alanine, glycine, asparagic acid, and phenylalanine. In a further particularly preferred embodiment, it can be advantageous if the pearl extract is additionally enriched with at least one or more of these amino acids. In the most preferred embodiment, the pearl extract is enriched with glutamic acid, serine, and leucine. In addition, depending on the extraction conditions, in particular, as a function of the extraction agent selection, a greater or lesser proportion of minerals and trace elements may reappear in the extract. A preferred extract contains organic and/or inorganic calcium salts as well as magnesium and sodium salts, inorganic silicon compounds, and/or phosphates. A very particularly preferred pearl extract contains at least 75%, preferably 85%, particularly preferably 90%, and very particularly preferably 95% of all the constituents of the naturally occurring pearls. Examples of pearl extracts usable according to the present invention are the commercial products Pearl Protein Extract BG® or Crodarom® Pearl.

The pearl extracts described above are contained preferably in a quantity from at least 0.01 to 20 wt %. The quantities of the extract used are preferably from 0.01 to 10 wt %, very particularly preferably 0.01 to 5 wt %, based on the entire two-component agent.

Although each of the conditioning substances recited in the various embodiments already yields a satisfactory result on its own, all embodiments in which preparation (B) contains multiple conditioning substances, including from different groups, are also encompassed within the scope of the present invention.

The two-component agent according to the present invention is packaged in different chambers of a multi-chamber tube. The multi-chamber tube is preferably a two-chamber tube, a first chamber receiving preparation (A) and a second chamber preparation (B). It is also possible, however, to use a multi-chamber tube that comprises more than two chambers, for example three or four chambers. In this case preparation (A) and/or preparation (B) can be distributed among several chambers of the multi-chamber tube, in which context care must of course be taken that exclusively preparation (A) or preparation (B) is present in a specific chamber.

Two-chamber tubes are already known in the existing art. In a particularly simple embodiment, the tubes have two separate chambers that are embodied as sleeves inserted into one another. These define the inner and the outer chamber, and terminate in the shared head region or emergence region. The head region is configured in such a way that the two preparations emerge together from the tube as soon as pressure is exerted on the latter. The configuration of the head region determines the stripe pattern in which the preparations emerge from the tube. The known commercially available tubes have an equal ratio for the volumes of the inner tube and outer tube, and thus a mixing ratio of 50:50. For products whose two phases must be stored separately and whose mixing ratio deviates from the conventional value of 50:50, the known tubes are not compatible.

The two-component agents according to the present invention are preferably packaged in a two-chamber tube that comprises an inner and an outer chamber that both terminate in a common or shared head region (emergence region). The head region is configured in such a way that the two preparations emerge together from the tube as soon as pressure is exerted on the latter. The configuration of this head region determines the pattern in which the preparations emerge from the tube.

Selection of the volumes of the individual chambers is based on the desired ratio between the volumes of preparation (A) and preparation (B) in the two-component agent. As a rule, the volumes are provided at a ratio that differs from the uniform distribution known hitherto. In this context, a "non-uniform distribution" is not to be understood as any kind of non-identical distribution of the volumes that exhibits a significant difference.

In addition to the feature of the different chamber volumes, the two-chamber tube that is preferably used is characterized by a particular configuration of the emergence region. There as well, the ratio of the chamber volumes is reflected in the cross sections of the pathways defined for the individual flows. In this context, it may be noted that the sub-flow of a preparation can exhibit multiple parallel branching flows. For example, separating means can divide the cross section of the pass-through conduit, at least approximately in accordance with the ratio, into two or more sub-flows. In this context, it may be noted that it is advantageous for the operation of the two-chamber tubes if the various components present in the respective tube chambers possess approximately the same viscosity.

In order to obtain mixing ratios conditioned by the formulation, and in the interest of uniform product emergence, geometries of the tube openings that exhibit a mixing ratio not equal to 50:50, namely from 80:20 to 60:40, preferably 75:25, are advantageous.

Although the invention is, in principle, intended not to be limited in any way with regard to the pattern with which the preparations emerge from the tube, it can be preferred according to the present invention if the first preparation emerges as a main strand and the second preparation forms multiple stripes running along that main strand. The invention is also not intended to be limited with regard to the number of such stripes. A number of from 2 to 4 stripes can, however, be particularly preferred according to the present invention for reasons of application engineering. In a first embodiment, preparation (A) can form the stripes, while preparation (B) forms the main strand; and in a second embodiment, preparation (B) forms the stripes while preparation (A) forms the main strand.

In a further embodiment, however, it can also be preferred if the two preparations together form the main strand in portions next to one another. In a further embodiment, the emerging strand can be made up of an inner region constituted by a first preparation, and an outer region constituted by the second preparation, the preparations also forming the emerging strand in accordance with their arrangement in the tube.

The quantitative ratio of preparation (A) to the quantity of preparation (B) is preferably, according to the present invention, in a range from 1:2 to 5:1. A quantitative ratio of 2:1 to 3:1 has proven to be very particularly preferred.

In principle, the present invention is intended to encompass any distribution of the chambers inside the tube. In a first embodiment, for example, the two individual chambers can be arranged next to one another in an outer casing. In an embodiment particularly preferred according to the present invention, the two-chamber tube comprises an inner tube that is entirely surrounded by an outer tube. This embodiment is characterized by optimally consistent metering of the two preparations. Although in principle any distribution of the preparations among the chambers of the tube is to be encompassed according to the present invention, it can be particularly preferred if preparation (A) is located in the outer tube, and preparation (B) in the inner tube.

The two-chamber tube is preferably produced from a material that is suitable for packaging tinting and dyeing agents of this type. Laminated aluminum has proven particularly suitable according to the present invention both for the outer walls and for the inner walls. Tubes made of plastic laminate (PE, PET, PP) or plastic coextrudates (PE, PET, PP) are, however, also conceivable. In addition, in an embodiment, the material of the inner tube can be selected independently of the material of the outer tube. A tube in which both the inner tube and the outer tube are produced from aluminum laminate has proven to be very particularly preferred according to the present invention. "Aluminum laminate" is understood according to the present invention to mean an aluminum layer coated with plastic.

In view of the fact that in the context of a tinting agent, the coloring preparation can account for a proportion of approximately 75%, and the conditioning preparation can account for a proportion of approximately 25%, and that the coloring preparation is, therefore, advantageously introduced into the outer tube having the larger volume, it is particularly advantageous if the shoulder region of the outer tube is reinforced with circular elements that exhibit particularly good barrier properties. In this context, it is advantageous to incorporate aluminum into the material of the circular elements.

In order to prevent emergence of the mixture during storage, and to ensure the consumer that the tube is undamaged, it is advantageous to seal the output opening with an authentication closure made of aluminum or plastic, which is removed by the consumer.

Furthermore, in addition to the essential components, preparations (A) and (B) can contain any active substances, additives, and adjuvants known for such preparations. In many cases the preparations contain at least one surfactant, both anionic as well as zwitterionic, ampholytic, and nonionic surfactants being suitable in principle. It has proven advantageous in many cases, however, to select the surfactants from anionic, zwitterionic, or nonionic surfactants.

All anionic surface-active substances suitable for application to the human body are suitable as anionic surfactants in the preparations according to the present invention. These are characterized by a water-solubility-creating anionic group such as, for example, a carboxylate, sulfate, sulfonate, or phosphate group, and a lipophilic alkyl group having approximately 10 to 22 C atoms. Glycol or polyglycol ether groups, ester, ether, and amide groups, and hydroxyl groups can additionally be contained in the molecule. Examples of suitable anionic surfactants are, in each case, in the form of the sodium, potassium, and ammonium as well as mono-, di-, and trialkanolammonium salts having 2 or 3 C atoms in the alkanol group:

linear fatty acids having 10 to 22 C atoms (soaps);
ethercarboxylic acids of the formula R—O—($CH_2$—$CH_2O$)$_x$—$CH_2$—COOH, in which R is a linear alkyl group having 10 to 22 C atoms and x=0 or is 1 to 16;
acylsarcosides having 10 to 18 C atoms in the acyl group;
acyltaurides having 10 to 18 C atoms in the acyl group;
acylisethionates having 10 to 18 C atoms in the acyl group;
sulfosuccinic acid mono- and -dialkyl esters having 8 to 18 C atoms in the alkyl group, and sulfosuccinic acid monoalkylpolyoxyethyl esters having 8 to 18 C atoms in the alkyl group and 1 to 6 oxyethyl groups;
linear alkanesulfonates having 12 to 18 C atoms;
linear alpha-olefinsulfonates having 12 to 18 C atoms;
alpha-sulfofatty acid methyl esters of fatty acids having 12 to 18 C atoms;
alkyl sulfates and alkylpolyglycol ether sulfates of the formula R—O($CH_2$—$CH_2O$)$_x$—$SO_3H$, in which R is a preferably linear alkyl group having 10 to 18 C atoms and x=0 or is 1 to 12;
mixtures of surface-active hydroxysulfonates according to DE A-37 25 030;
sulfated hydroxyalkylpolyethylene and/or hydroxyalkylenepropylene glycol ethers according to DE-A-37 23 354;
sulfonates of unsaturated fatty acids having 12 to 24 C atoms and 1 to 6 double bonds, according to DE-A-39 26 344;
esters of tartaric acid and citric acid with alcohols that represent addition products of approximately 2-15 molecules ethylene oxide and/or propylene oxide with fatty alcohols having 8 to 22 C atoms.

Preferred anionic surfactants are alkyl sulfates, alkylpolyglycol ether sulfates, and ethercarboxylic acids having 10 to 18 C atoms in the alkyl group and up to 12 glycol ether groups in the molecule, as well as, in particular, salts of saturated and, in particular, unsaturated $C_8$-$C_{22}$ carboxylic acids, such as oleic acid, stearic acid, isostearic acid, and palmitic acid.

Nonionogenic surfactants contain as a hydrophilic group, for example, a polyol group, a polyalkylene glycol ether group, or a combination of a polyol and polyglycol ether group. Such compounds are, for example:
addition products of 2 to 30 mol ethylene oxide and/or 1 to 5 mol propylene oxide with linear fatty alcohols having 8 to 22 C atoms, with fatty acids having 12 to 22 C atoms, and with alkylphenols having 8 to 15 C atoms in the alkyl group;
$C_{12}$-$C_{22}$ fatty acid mono- and diesters of addition products of 1 to 30 Mol ethylene oxide with glycerol;
$C_8$-$C_{22}$ alkylmono- and -oligoglycosides and their ethoxylated analogs; and
addition products of 5 to 60 mol ethylene oxide with castor oil and hydrogenated castor oil.

Preferred nonionic surfactants are alkylpolyglycosides of the general formula $R^1O$-$(Z)_x$. These compounds are characterized by the following parameters: The alkyl radical $R^1$ contains 6 to 22 carbon atoms and can be both linear and branched. Primary linear radicals, and aliphatic radicals that are methyl-branched in the 2- position, are preferred. Such alkyl radicals are, for example, 1-octyl, 1-decyl, 1-lauryl, 1-myristyl, 1-cetyl, and 1-stearyl. 1-octyl, 1-decyl, 1-lauryl, 1-myristyl are particularly preferred. When so-called "oxo alcohols" are used as starting materials, compounds having an odd number of carbon atoms in the alkyl chain predominate.

The alkylpolyglycosides usable according to the present invention can, for example, contain only one specific alkyl radical $R^1$. Usually, however, these compounds are produced from natural fats and oils or mineral oils. In this case mixtures corresponding to the starting compounds, or corresponding to the respective processing of those compounds, are present as alkyl radicals R.

Particularly preferred are those alkylpolyglycosides in which $R^1$ is made up
substantially of $C_8$ and $C_{10}$ alkyl groups,
substantially of $C_{12}$ and $C_{14}$ alkyl groups,
substantially of $C_8$ to $C_{16}$ groups,
substantially of $C_{12}$ to $C_{16}$ alkyl groups.

Any mono- or oligosaccharides can be used as a sugar module Z. Sugars having 5 or 6 carbon atoms, as well as the corresponding oligosaccharides, are usually used. Such sugars are, for example, glucose, fructose, galactose, arabinose, ribose, xylose, lyxose, allose, altrose, mannose, gulose, idose, talose and sucrose. Preferred sugar modules are glucose, fructose, galactose, arabinose and sucrose; glucose is particularly preferred.

The alkylpolyglysosides usable according to the present invention contain, on average, 1.1 to 5 sugar units. Alkylpolyglycosides having x values from 1.1 to 1.6 are preferred. Alkylglycosides in which x=1.1 to 1.4 are particularly preferred.

In addition to their surfactant effect, the alkylglycosides can also serve to improve the fixing of scent components on the hair. In cases where an action of the perfume oil on the hair that goes beyond the duration of the hair treatment is desired, one skilled in the art will, therefore, preferably resort to this substance class as a further ingredient of the preparations according to the present invention.

The alkoxylated homologs of the aforesaid alkylpolyglycosides can also be used according to the present invention. These homologs can contain, on average, up to 10 ethylene oxide and/or propylene oxide units per alkylglycoside unit.

Zwitterionic surfactants can furthermore be utilized, in particular, as co-surfactants. "Zwitterionic surfactants" refers to those surface-active compounds that contain in the molecule at least one quaternary ammonium group and at least one —COO$^{(-)}$ or —SO3$^{(-)}$ group. Particularly suitable zwitterionic surfactants are the so-called betaines, such as the N-alkyl-N,N-dimethylammonium glycinates, for example, cocalkyldimethylammonium glycinate, N-acylaminopropyl-N,N-dimethylammonium glycinates, for example, cocacylaminopropyldimethylammonium glycinate, and 2-alkyl-3-carboxymethyl-3-hydroxy-ethylimidazolines, having in each case 8 to 18 C atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

Ampholytic surfactants are likewise suitable, in particular, as co-surfactants. "Ampholytic surfactants" are understood to be those surface-active compounds that contain in the molecule, in addition to a $C_8$-$C_{18}$ alkyl or acyl group, at least one free amino group and at least one —COOH or —SO$_3$H group, and are suitable for the formation of internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropyl-glycines, N-alkyltaurines, N-alkylsarcosines, 2-alkylaminopropionic acids, and alkylaminoacetic acids, having in each case 8 to 18 C atoms in the alkyl group. Particularly preferred ampholytic surfactants are N-cocalkylaminopropionate, cocacylaminoethylamino-propionate, and $C_{12-18}$ acylsarcosine.

The compounds having alkyl groups used as a surfactant can in each case be uniform substances. It is preferred as a rule, however, to begin with natural plant or animal raw materials when producing these substances, so that substance mixtures having different alkyl chain lengths as a function of the respective raw material are obtained.

In the case of the surfactants that represent addition products of ethylene oxide and/or propylene oxide with fatty alcohols, or derivatives of these addition products, both products having a "normal" homolog distribution and those having a restricted homolog distribution can be used. A "normal" homolog distribution is understood to mean mixtures of homologs that are obtained upon the reaction of fatty alcohol and alkylene oxide using alkali metals, alkali metal hydroxides, or alkali metal alcoholates as catalysts. Restricted homolog distributions, on the other hand, are obtained when, for example, hydrotalcites, alkaline-earth metal salts of ethercarboxylic acids, or alkaline-earth metal oxides, hydroxides, or alcoholates are used as catalysts. The use of products having a restricted homolog distribution can be preferred.

The preparations according to the present invention can further contain additional active substances, additives, and adjuvants such as, for example:
  nonionic polymers such as, for example, vinylpyrrolidone/vinyl acrylate copolymers, polyvinylpyrrolidone and vinylpyrrolidone/vinyl acetate copolymers and polysiloxanes;
  zwitterionic and amphoteric polymers such as, for example, acrylamidopropyltrimethylammonium chloride/acrylate copolymers and octylacrylamide/methyl methacrylate/tert.-butylaminoethyl methacrylate/2-hydroxypropyl methacrylate copolymers;
  anionic polymers such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methylvinyl ether/maleic acid anhydride copolymers, and acrylic acid/ethyl acrylate/n-tert.-butylacrylamide terpolymers;
  thickening agents such as agar-agar, guar gum, alginates, xanthan gum, gum arabic, karaya gum, locust bean flour, linseed gums, dextrans, cellulose derivatives, e.g., methyl cellulose, hydroxyalkyl cellulose, and carboxymethyl cellulose, starch fractions and derivatives such as amylose, amylopectin, and dextrins, clays such as, for example, bentonite, or entirely synthetic hydrocolloids such as, for example, poly(vinylalcohol);
  structuring agents such as maleic acid and lactic acid;
  perfume oils, dimethylisosorbide, and cyclodextrins;
  solvents and solubilizers such as ethanol, isopropanol, ethylene glycol, propylene glycol, glycerol, and diethylene glycol;
  quaternized amines such as methyl-1-alkylamidoethyl-2-alkylimidazolinium methosulfate;
  defoamers such as silicones;
  dyes for coloring the agent;
  anti-dandruff ingredients such as Piroctone Olamine, Zinc Omadine, and climbazole; substances for adjusting pH, such as, for example, usual acids, in particular, edible acids, and bases;
  cholesterol;
  consistency agents such as sugar esters, polyol esters, or polyolalkyl ethers;

fats and waxes such as spermaceti, beeswax, montan wax, and paraffins;

fatty acid alkanolamides;

complex-forming agents such as EDTA, NTA, β-alaninediacetic acid, and phosphonic acids;

swelling and penetrating substances, such as glycerol, propylene glycol monoethyl ether, carbonates, hydrogencarbonates, guanidines, ureas, and primary, secondary, and tertiary phosphates;

opacifiers such as styrene/PVP and styrene/acrylamide copolymers;

pearlescent agents such as ethylene glycol mono- and distearate, as well as PEG-3 distearate;

pigments;

preservatives;

antioxidants.

With regard to further optional components as well as the quantities of those components that are used, reference is made expressly to the relevant manuals known to those skilled in the art, for example, K. H. Schrader, Grundlagen und Rezepturen der Kosmetika [Cosmetic fundamentals and formulations], 2nd ed., Hüthig Buch Verlag Heidelberg, 1989.

The preparations according to the present invention contain the components essential to the invention preferably in a suitable aqueous, alcoholic, or aqueous/alcoholic carrier. For hair dyeing purposes, such carriers are, for example, cremes, emulsions, gels, or also surfactant-containing foaming solutions such as, for example, shampoos or other preparations that are suitable for application to the hair.

For purposes of the present invention, "aqueous/alcoholic solutions" are understood to be aqueous solutions containing 3 to 70 wt % of a $C_1$-$C_4$ alcohol, in particular, ethanol or isopropanol. The agents according to the present invention can additionally contain further organic solvents such as, for example, methoxybutanol, benzyl alcohol, ethyl diglycol, or 1,2-propylene glycol. All water-soluble organic solvents are preferred in this context.

Furthermore, the two-component agents according to the present invention can contain a reducing agent. Examples of reducing agents preferred according to the present invention are sodium sulfite, ascorbic acid, thioglycolic acid and its derivatives, sodium thionite, alkali metal citrate salts, and N-acetyl-L-cysteine. Very particularly preferred reducing agents are alkali metal citrate salts, in particular sodium citrate, and N-acetyl-L-cysteine. N-acetyl-L-cysteine is a very particularly preferred reducing agent.

The agents according to the present invention can furthermore contain alkalizing agents, usually alkaline or alkaline-earth hydroxides, ammonia, or organic amines. Preferred alkalizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol, and triethanolamine, as well as alkali metal and alkaline-earth metal hydroxides. Monoethanolamine, triethanolamine, and 2-amino-2-methylpropanol and 2-amino-2-methyl-1,3-propanediol are preferred in particular in the context of this group. The use of ω-amino acids, such as ω-aminohexanoic acid, as an alkalizing agent is also possible.

The two-component agents according to the present invention can additionally contain, in preparation (A) and/or in preparation (B), pearlescent pigments for coloring. Pearlescent pigments preferred according to the present invention are natural pearlescent pigment such as, for example, fish silver (mixed guanine/hypoxanthine crystals from fish scales) or nacre (from ground mussel shells), monocrystalline pearlescent pigments such as, for example, bismuth oxychloride, as well as pearlescent pigments based on mica or mica/metal oxide. The last-mentioned pearlescent pigments are equipped with a metal oxide coating. With the use of pearlescent pigments, gloss and, if applicable, additionally color effects are achieved in the two-component agents according to the present invention. The color imparted by way of the pearlescent pigments used in the two-component agents does not, however, influence the color that results from dyeing the keratin fibers.

Mica-based and mica/metal oxide-based pearlescent pigments are likewise preferred according to the present invention. Mica is one of the layered silicates. The most important representatives of these silicates are muscovite, phlogopite, paragonite, biotite, lepidolite, and margarite. For production of the pearlescent pigments in combination with metal oxides, the mica (predominantly muscovite or phlogopite) is coated with a metal oxide. Suitable metal oxides are, among others, $TiO_2$, $Cr_2O_3$, and $Fe_2O_3$. Appropriate coating causes interference pigments as well as gloss-color pigments to be obtained as pearlescent pigments according to the present invention.

The particle size of the pearlescent pigments that are preferably used is preferably between 1.0 and 100 μm, particularly preferably, between 5.0 and 60.0 μm.

Particularly preferred pearlescent pigments are pigments that are marketed by the Merck company under the trade names Colorona® the pigments Colorona® Red-Brown (47-57 wt % Muscovite Mica ($KH_2(AlSiO_4)_3$), 43-50 wt % $Fe_2O_3$ (INCI: Iron Oxides CI 77491), <3 wt % $TiO_2$ (INCI: Titanium Dioxide CI 77891)), Colorona® Blackstar Blue (39-47 wt % Muscovite Mica ($KH_2(AlSiO_4)_3$), 53-61 wt % $Fe_3O_4$ (INCI: Iron Oxides CI 77499)), Colorona° Siena Fine (35-45 wt % Muscovite Mica ($KH_2(AlSiO_4)_3$), 55-65 wt % $Fe_2O_3$ (INCI: Iron Oxides CI 77491)), Colorona® Aborigine Amber (50-62 wt % Muscovite Mica ($KH_2(AlSiO_4)_3$), 36-44 wt % $Fe_3O_4$ (INCI: Iron Oxides CI 77499), 2-6 wt % $TiO_2$ (INCI: Titanium Dioxide CI 77891)), Colorona® Patagonian Purple (42-54 wt % Muscovite Mica ($KH_2(AlSiO_4)_3$), 26-32 wt % $Fe_2O_3$ (INCI: Iron Oxides CI 77491), 18-22 wt % $TiO_2$ (INCI: Titanium Dioxide CI 77891), 2-4 wt % Prussian blue (INCI: Ferric Ferrocyanide CI 77510)), Colorona® Chameleon (40-50 wt % Muscovite Mica ($KH_2(AlSiO_4)_3$), 50-60 wt % $Fe_2O_3$ (INCI: Iron Oxides CI 77491)), and Silk® Mica (>98 wt % Muscovite Mica ($KH_2(AlSiO_4)_3$)) being very particularly preferred.

Regarding the pearlescent pigments usable in the two-component agents according to the present invention, reference is further expressly made to the monographs Inorganic Pigments, Chemical technology review No. 166, 1980, pp. 161-173 (ISBN 0-8155-0811-5), and Industrial Inorganic Pigments, 2nd ed., Weinheim, VCH, 1998, pp. 211-231.

If preparation (A) contains a precursor of a nature-analogous dye, oxidative color development can, in principle, be accomplished with atmospheric oxygen. In a specific embodiment of this subject matter, however, the emerging application preparation can also be additionally mixed, immediately before application, with a preparation containing an oxidizing agent. Suitable as oxidizing agents are persulfates, chlorites, and, in particular, hydrogen peroxide or its addition products with urea, melamine, or sodium borate. It is preferable, however, to dispense with the addition of a chemical oxidizing agent.

The actual tinting and/or dyeing agent is obtained by intermixing of the two preparations (A) and (B) emerging from the tube. This intermixing of the preparations (A) and (B) emerging separately from the tube can be accomplished both before application on the fibers in a separate step, and as a side effect as the emerging strand is worked into the fibers. The ready-to-use preparation that results should preferably exhibit a pH in the range from 6 to 12, in particular, from 8 to 10. If not otherwise noted, the indications as to pH in the context of the present disclosure are understood to mean the pH at 25° C. Application of the hair-dyeing agents in a weakly alkaline medium is particularly preferred. Application temperatures can be in a range between 15 and 40° C. After a residence time of 5 to 45 minutes, the hair-dyeing agent is removed, by rinsing, from the hair that is to be dyed. Subsequent washing with a shampoo is superfluous if a highly surfactant-containing carrier, e.g., a dyeing shampoo, was used.

Preparations (A) and (B) according to the present invention preferably exhibit viscosities in the range from 2,000 to 200,000 mPa, in particular from 5,000 to 50,000 mPa (Brookfield viscosimeter, No. 4 spindle, 20 rpm, 20° C.). This ensures that the two-component agent exhibits good mixability and that the emergence pattern nevertheless possesses sufficient stability.

A further subject of the present invention is a method for tinting keratinic fibers, in particular, human hair, in which a two-component agent according to the present invention is squeezed out of the tube, the application preparation is applied onto the fibers, and after a residence time it is rinsed off again.

The examples that follow are intended to explain the subject matter of the present application without limiting it.

EXEMPLIFYING EMBODIMENTS

The following formulations were produced. The quantities indicated are understood, unless otherwise indicated, to be as percentages by weight.

Formulations of Preparations (A)

| Raw Material | Tinting Creme 1 (Copper Blonde) | Tinting Creme 2 (Violet) |
| --- | --- | --- |
| Sodium laureth sulfate, 27% in H₂O | 8.00 | 8.00 |
| Aqueous ammonium carbopol solution, 1% | 35.00 | 35.00 |
| Lowenol ® C-279 | 0.50 | — |
| Cetyl alcohol | 2.00 | 2.00 |
| Polawax ® GP 200 | 1.50 | 1.50 |
| Lanette ® 14 | 1.20 | 1.20 |
| Paraffin oil DAB9 | 1.00 | 1.00 |
| Emulgade ® 1000NI | 3.50 | 3.50 |
| Ethyl diglycol | 1.00 | 1.00 |
| Methoxybutanol | 5.00 | — |
| Benzyl alcohol | 0.50 | 1.00 |
| Tetrasodium EDTA | 0.15 | 0.15 |
| HC Red No. 3 | 0.70 | 0.60 |
| Violet 1,4 D | 0.01 | — |
| HC Yellow No. 2 | 0.30 | — |
| 6-Chloro-4-nitro-2-aminophenol | 0.15 | — |
| HC Blue No. 2 | — | 0.6 |
| Basic Blue 99 | — | 0.1 |
| 2-Amino-2-methylpropanol | q.s.p. pH 10 | q.s.p. pH 10 |
| Perfume | 0.20 | 0.20 |
| Water | q.s.p. 100 | q.s.p. 100 |

| Raw material | Tinting creme 3 (Red) | Tinting creme 4 (Red-Brown) |
| --- | --- | --- |
| Cetyl stearyl alcohol | 8.00 | 8.00 |
| Glycerol monostearate | 1.50 | 1.50 |
| Isopropyl myristate | 3.50 | 3.50 |
| Laureth-23 | 0.40 | 0.40 |
| Ceteareth-30 | 1.00 | 1.00 |
| Lanette ® 14 | 1.20 | 1.20 |
| Cutina ® HR | 1.00 | 1.00 |
| Ethyl diglycol | 1.00 | 1.00 |
| Methoxybutanol | 5.00 | — |
| Benzyl alcohol | 0.50 | 1.00 |
| Tetrasodium EDTA | 0.15 | 0.15 |
| HC Red No. 3 | 0.01 | 0.6 |
| HC Yellow No. 12 | 0.15 | — |
| HC Yellow No. 2 | 0.10 | 0.20 |
| 6-Chloro-4-nitro-2-aminophenol | 0.06 | 0.08 |
| HC Blue No. 2 | 0.50 | 0.40 |
| Basic Blue 99 | — | 0.01 |
| N,N-Bis(2-hydroxyethyl-methyl)amino-5-nitrobenzene | — | 0.15 |
| 2-Amino-2-methylpropanol | q.s.p. pH 10 | q.s.p. pH 10 |
| Perfume | 0.20 | 0.20 |
| Water | q.s.p. 100 | q.s.p. 100 |

| Raw material | Tinting creme 5 (Red) | Tinting creme 6 (Brown) |
| --- | --- | --- |
| Cetyl stearyl alcohol | 8.00 | 8.00 |
| Covasterol | 0.50 | 0.50 |
| Isopropyl myristate | 3.40 | 3.40 |
| Laureth-23 | 0.30 | 0.30 |
| Cutina ® HR | 0.80 | 0.80 |
| Myristyl alcohol | 1.00 | 1.00 |
| Ceteareth-30 | 1.00 | 1.00 |
| Propylene glycol | 4.00 | 3.00 |
| Benzyl alcohol | 0.50 | 0.50 |
| Tetrasodium EDTA | 0.30 | 0.30 |
| HC Red No. 3 | 1.30 | — |
| Violet 1,4 D | 0.002 | — |
| N,N-Bis(2-hydroxyethyl)-2-nitro-p-phenylenediamine | — | 1.00 |
| 4-Amino-3-nitrophenol | — | 0.02 |
| HC Blue No. 2 | — | 1.50 |
| Basic Blue 99 | — | 0.50 |
| HC Yellow No. 2 | — | 0.10 |
| 2-Amino-2-methylpropanol | q.s.p. pH 9.5 | q.s.p. pH 9.5 |
| Perfume | 0.30 | 0.30 |
| Water | q.s.p. 100 | q.s.p. 100 |

| Raw material | Tinting creme 7 (Copper) | Tinting creme 8 (Ash blonde) |
| --- | --- | --- |
| Cetyl stearyl alcohol | 8.00 | 8.00 |
| Covasterol | 0.50 | 0.50 |
| Isopropyl myristate | 3.40 | 3.40 |
| Laureth-23 | 0.30 | 0.30 |
| Cutina ® HR | 0.80 | 0.80 |
| Myristyl alcohol | 1.00 | 1.00 |
| Ceteareth-30 | 1.00 | 1.00 |
| Cetyltrimethylammonium chloride, 25% | 9.00 | 9.00 |
| Propylene glycol | 4.00 | 2.00 |
| Benzyl alcohol | 0.80 | 0.30 |
| Tetrasodium EDTA | 0.30 | — |
| N,N-Bis(2-hydroxyethyl)-2-nitro-p-phenylenediamine | 0.02 | — |
| HC Blue No. 2 | — | 0.05 |
| HC Yellow No. 2 | 0.30 | — |
| 2-Amino-6-chloro-4-nitrophenol | 0.20 | — |
| 4-Hydroxypropylamino-3-nitrophenol | 0.50 | — |
| 2-Amino-2-methylpropanol | q.s.p. pH 9.0 | q.s.p. pH 9.5 |
| Perfume | 0.20 | 0.40 |
| Water | q.s.p. 100 | q.s.p. 100 |

| Raw material | Tinting creme 9 (Orange) | Tinting creme 10 (Fawn) |
| --- | --- | --- |
| Cetyl stearyl alcohol | 8.00 | 8.00 |
| Covasterol | 0.50 | 0.50 |
| Isopropyl myristate | 3.40 | 3.40 |
| Laureth-23 | 0.30 | 0.30 |

-continued

| | | |
|---|---|---|
| Cutina ® HR | 0.80 | 0.80 |
| Myristyl alcohol | 1.00 | 1.00 |
| Ceteareth-30 | 1.00 | 1.00 |
| Cetyltrimethylammonium chloride, 25% | 9.00 | 9.00 |
| Propylene glycol | — | 3.00 |
| Benzyl alcohol | 0.50 | 0.50 |
| Tetrasodium EDTA | 0.30 | 0.30 |
| HC Blue No. 2 | — | 0.80 |
| HC Yellow No. 2 | — | 0.20 |
| 2-Amino-6-chloro-4-nitrophenol | — | 0.15 |
| HC Red No. 15 | — | 0.20 |
| HC Yellow No. 13 | 0.02 | 0.05 |
| Basic Yellow 87 | 0.20 | — |
| Basic Orange 31 | 0.05 | — |
| 2-Amino-2-methylpropanol | q.s.p. pH 9.0 | q.s.p. pH 9.5 |
| Perfume | 0.30 | 0.30 |
| Water | q.s.p. 100 | q.s.p. 100 |

| Raw material | Tinting creme 11 (Yellow) |
|---|---|
| Cetyl stearyl alcohol | 8.00 |
| Covasterol | 0.50 |
| Isopropyl myristate | 3.40 |
| Laureth-23 | 0.30 |
| Cutina ® HR | 0.80 |
| Myristyl alcohol | 1.00 |
| Ceteareth-30 | 1.00 |
| Cetyltrimethylammonium chloride, 25% | 9.00 |
| Propylene glycol | 3.00 |
| Benzyl alcohol | 0.80 |
| Tetrasodium EDTA | 0.30 |
| Basic Orange 31 | 0.01 |
| Basic Red 51 | 0.20 |
| 2-Amino-2-methylpropanol | q.s.p. pH 9.5 |
| Perfume | 0.30 |
| Water | q.s.p. 100 |

Formulations of Preparations (B).

| Raw material | Conditioning creme A | Conditioning creme B |
|---|---|---|
| Sodium laureth sulfate, 27% in H₂O | 8.00 | 8.00 |
| Aqueous ammonium carbopol solution, 1% | 35.00 | 35.00 |
| Cetyl alcohol | 2.00 | 2.00 |
| Polawax ® GP 200 | 1.50 | 1.50 |
| Lanette ® 14 | 1.20 | 1.20 |
| Paraffin oil DAB9 | 1.00 | 1.00 |
| Emulgade ® 1000NI | 3.50 | 3.50 |
| Merquat ® 100 | 1.00 | 1.00 |
| Panthenol | — | 0.50 |
| Crosilk ® Liquid | 0.50 | — |
| 2-Amino-2-methylpropanol | q.s.p. pH 9 | — |
| Citric acid | — | q.s.p. pH 6.5 |
| Propylene glycol | — | 4.00 |
| p-Hydroxybenzoic acid methyl ester | — | 0.15 |
| Perfume | 0.20 | — |
| Water | q.s.p. 100 | q.s.p. 100 |

| Raw material | Conditioning creme C | Conditioning creme D |
|---|---|---|
| Cetyl stearyl alcohol | 8.00 | 8.00 |
| Glycerol monostearate | 1.50 | 1.50 |
| Isopropyl myristate | 3.50 | 3.50 |
| Ceteareth-30 | 1.00 | 1.00 |
| Lanette ® 14 | 1.20 | 1.20 |
| Cutina ® HR | 1.00 | — |
| Merquat ® 100 | 1.00 | 1.00 |
| Panthenol | — | 0.50 |
| Vitamin B6 | 0.50 | — |
| 2-Amino-2-methylpropanol | q.s.p. pH 9 | — |
| Citric acid | — | q.s.p. pH 6.5 |
| Propylene glycol | — | 4.00 |
| p-Hydroxybenzoic acid methyl ester | — | 0.15 |
| MICA | — | 0.10 |
| Perfume | 0.20 | — |
| Water | q.s.p. 100 | q.s.p. 100 |

| Raw material | Conditioning creme E | Conditioning creme F | Conditioning creme G |
|---|---|---|---|
| Cetyl stearyl alcohol | 6.50 | 8.00 | 7.00 |
| Covasterol | 0.30 | 0.40 | 0.40 |
| Isopropyl myristate | 2.90 | 3.00 | 3.00 |
| Laureth-23 | 0.20 | 0.25 | 0.20 |
| Cutina ® HR | 0.65 | 0.80 | 0.70 |
| Myristyl alcohol | 0.80 | 0.90 | 0.90 |
| Ceteareth-30 | 0.80 | 0.90 | 0.90 |
| Cetyltrimethylammonium chloride, 25% | 9.00 | 9.00 | 9.00 |
| Propylene glycol | — | — | 1.00 |
| Tetrasodium EDTA | 0.30 | — | 0.30 |
| Vitamin B6 | 1.00 | — | — |
| Merquat ® Plus 3330 | — | 1.00 | — |
| Serine | — | — | 1.00 |
| 2-Amino-2-methylpropanol | q.s.p. pH 8.0 | q.s.p. pH 9.0 | q.s.p. pH 8.0 |
| Perfume | 0.20 | 0.20 | — |
| Water | q.s.p. 100 | q.s.p. 100 | q.s.p. 100 |

Coloring Tests.

Tinting cremes 1 and 2 were each packaged in a two-chamber tube together with conditioning creme A and B, respectively, at a ratio of 3:1. The inner tube contained preparation (B), and the outer tube preparation (A). The entire tube was made of aluminum laminate.

The resulting two-component agents were squeezed respectively out of the tubes and applied directly onto human hair (Kerling Co., natural white). The application preparation was massaged into the hair, left there for 30 minutes at room temperature, and then rinsed out. Intense copper and violet shades, respectively, were obtained after the hair dried.

An analogous procedure was used with tinting cremes 3 and 4 and conditioning cremes C and D, respectively. Intense caramel and red-brown shades, respectively, were obtained in this case.

An analogous procedure was likewise used with tinting cremes 5 to 11 and conditioning cremes E, F and G. The color shades obtained are evident from the Tables above.

List of Commercial Products Used.

The commercial products used in the context of the examples are defined as follows:

| | |
|---|---|
| Carbopol | Polyacrylic acid (INCI name: Carbomer) (Noveon) |
| Covasterol | (INCI name: Glyceryl Isostearate, Isostearyl Alcohol, Beta-Sitosterol, Butyrospermum Parkii (Shea Butter), Euphorbia Cerifera (Candelilla) Wax) (LCW) |
| Crosilk ® Liquid | Approx. 27-31% solids (INCI name: Aqua, Silk Amino Acids) (Croda) |
| Cutina ® HR | Hydrogenated castor oil (INCI name: Hydrogenated Castor Oil) (Cognis) |
| Emulgade ® 1000NI | (INCI name: Cetearyl Alcohol, Ceteareth-20) (Cognis) |
| Lanette ® 14 | Myristyl alcohol (INCI name: Myristyl Alcohol) (Cognis) |

-continued

| Lowenol ® C-279 | C16-18 fatty alcohol having approx. 2 EO units (INCI name: Ceteareth-2) (Lowenstein) |
| --- | --- |
| Merquat ® 100 | Poly(dimethyldiallylammonium chloride) (approx. 40% solids; INCI name: Polyquaternium-6) (Ondeo Nalco) |
| Merquat ® Plus 3330 | Polymeric quaternary ammonium salt based on acrylic acid, Dimethyldiallylammonium chloride, and acrylamide (INCI name: Polyquaternium-39) (Nalco) |
| Polawax ® GP 200 | (INCI name: Cetearyl Alcohol, PEG-20 Stearate) (Croda) |
| Violet 1,4 D | 1,4-Bis[(2'-hydroxyethyl)-amino]-2-nitrobenzene |

The invention claimed is:

1. A two-component agent for tinting and/or dyeing keratinic fibers comprising a first preparation (A) comprising at least one direct-absorbing dye and/or at least one precursor of a nature-analogous dye, and a second preparation (B) comprising at least one conditioning substance, wherein the first and second preparations are packaged separately from one another in a two chamber tube having an inner and outer chamber and a common exit region wherein the exit region is configured in such a way that the first preparation exits as the main strand and the second preparation forms a plurality of stripes running along the main strand when pressure is exerted on the tube and wherein the ratio of preparation (A) to preparation (B) is in the range of 2:1 to 3:1.

2. The agent of claim 1 wherein the preparation (A) is comprised of at least one direct-absorbing dye that is selected from the group consisting of nitrophenylenediamines, nitroaminophenols, azo dyes, anthraquinones, and indophenols.

3. The agent of claim 1 wherein the preparation (A) is further comprised of least one cationic direct-absorbing dye.

4. The agent of claim 1 wherein the preparation (A) is further comprised of at least one vegetable dye.

5. The agent of claim 1 wherein the precursor of a nature-analogous dye is an indole derivative and/or an indoline derivative.

6. The agent of claim 1 wherein the conditioning substance is a cationic surfactant.

7. The agent of claim 1 wherein the conditioning substance is a conditioning polymer.

8. The agent of claim 1 further comprising a UV filter.

9. The agent of claim 1 wherein the conditioning substance is a vitamin, a provitamin, a vitamin precursor, and/or one or more derivatives thereof.

10. The agent of claim 1 further comprising a plant extract.

11. The agent of claim 1 wherein the preparation (B) is further comprised of a protein hydrolysate and/or a derivative thereof.

12. The agent of claim 1 wherein the conditioning comprises at least one compound selected from the group consisting of ectoin or ectoin derivatives, allantoin, taurine, and bisabolol.

13. The agent of claim 1 wherein the conditioning substance is a mono- or oligosaccharide.

14. The agent of claim 1 wherein the conditioning substance is a silicone oil and/or one silicone gum.

15. The agent of claim 1 wherein the conditioning substance is an oily substance.

16. A tube comprising a first and second chamber each chamber having one opening, wherein the first chamber is comprised of a preparation (A) comprising at least one direct-absorbing dye and/or at least one precursor of a nature-analogous dye, and a second chamber comprising a preparation (B) comprising at least one conditioning substance wherein the chamber openings are oriented in such a way that the contents of each of the first and second chambers is emitted simultaneously into a common space wherein the preparations are emitted from the tube at a volume ratio of (A) to (B) corresponding to 1:2 to 5:1.

17. The tube of claim 16 wherein the preparations are emitted from the tube in a stripe-like pattern.

18. A method for tinting keratinic fibers in particular human hair comprising contacting the fibers with preparation (A) and (B) from the tube of claim 16 for a period of time and then removing the preparations from the fibers.

19. The method of claim 18 wherein the preparations are removed by rinsing.

* * * * *